(12) United States Patent
Nishio et al.

(10) Patent No.: US 7,562,555 B2
(45) Date of Patent: Jul. 21, 2009

(54) WATER-REPELLENT FILTER, A METHOD OF MANUFACTURING A WATER-REPELLENT FILTER MEMBER, AND GAS SENSOR

(75) Inventors: Hisaharu Nishio, Aichi (JP); Yuichi Yamada, Aichi (JP); Masahiro Asai, Aichi (JP); Makoto Hishiki, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 762 days.

(21) Appl. No.: 11/168,443

(22) Filed: Jun. 29, 2005

(65) Prior Publication Data

US 2007/0017193 A1    Jan. 25, 2007

(30) Foreign Application Priority Data

Jun. 30, 2004    (JP) .............................. 2004-194383

(51) Int. Cl.
*B01D 17/12* (2006.01)
*B65D 51/16* (2006.01)
*B65D 53/00* (2006.01)

(52) U.S. Cl. ............................ 73/23.2; 96/420; 96/421; 96/422; 96/423; 96/417; 55/385.4; 73/23.41; 73/24.06; 73/29.04; 422/83; 422/105; 422/107; 422/108

(58) Field of Classification Search ................... 96/417, 96/420–423; 55/385.4; 210/85, 103, 443; 277/650, 928; 220/203.13, 801, 371; 73/23.2, 73/23.41, 24.06, 29.04; 422/82, 105, 107, 422/108
See application file for complete search history.

(56) References Cited

U.S. PATENT DOCUMENTS

| | | | | |
|---|---|---|---|---|
| 5,891,223 A | * | 4/1999 | Shaw et al. .................... | 96/134 |
| 5,914,415 A | * | 6/1999 | Tago .......................... | 55/385.4 |
| 6,395,050 B1 | * | 5/2002 | Wickland et al. .......... | 55/385.4 |
| 6,471,853 B1 | * | 10/2002 | Moscaritolo ................. | 210/85 |
| 6,500,322 B2 | | 12/2002 | Akatsuka et al. | |
| 6,679,099 B2 | | 1/2004 | Fujita et al. | |
| 6,852,216 B2 | * | 2/2005 | Moscaritolo et al. ......... | 210/85 |
| 7,166,024 B2 | * | 1/2007 | Mashiko et al. ............. | 454/370 |
| 7,255,354 B2 | * | 8/2007 | Tamura et al. .............. | 277/650 |

FOREIGN PATENT DOCUMENTS

| | | |
|---|---|---|
| JP | 2000-298113 | 10/2000 |
| JP | 2001-133431 | 5/2001 |
| JP | 2001-208724 | 8/2001 |

(Continued)

*Primary Examiner*—Duane Smith
*Assistant Examiner*—Minh-Chau T Pham
(74) *Attorney, Agent, or Firm*—Sughrue Mion, PLLC

(57) ABSTRACT

A water-repellent filter member formed from a resin sheet of a porous, fibrous structure having air permeability and water repellency; a waterproof instrument and gas sensor having air permeability; and a method of manufacturing the same. A water-repellent filter member (19) is formed from a resin sheet (54) of a porous, fibrous structure having air permeability and water repellency by subjecting the resin sheet to forming work, and includes an axially extending tubular side wall portion (19s) and a bottom wall portion closing one end of the tubular side wall portion. At least a portion of the bottom wall portion (19t) retains the porous, fibrous structure of the resin sheet and thereby has air permeability.

3 Claims, 11 Drawing Sheets

FOREIGN PATENT DOCUMENTS

| | | |
|---|---|---|
| JP | 2002-39985 | 2/2002 |
| JP | 2002-90336 | 3/2002 |
| JP | 2002-116176 | 4/2002 |
| JP | 2002-181765 | 6/2002 |
| JP | 2002-181766 | 6/2002 |
| JP | 2002-286686 | 10/2002 |
| JP | 2002-372513 | 12/2002 |
| JP | 2003-194765 | 7/2003 |

* cited by examiner

WATER-REPELLENT FILTER, A METHOD OF MANUFACTURING A WATER-REPELLENT FILTER MEMBER, AND GAS SENSOR

BACKGROUND OF THE INVENTION

1. Field of the Invention

The present invention relates to a water-repellent filter member and a method of manufacturing the water-repellent filter member, as well as to a waterproof instrument using the water-repellent filter member, and a gas sensor using the water-repellent filter member.

2. Description of the Related Art

Among instruments having an internal space, certain instruments allow air communication between the internal space and the exterior thereof via an air vent or the like. Unless appropriate measures are taken against entry of water, there is a risk of water entering into the internal space via the air vent in association with entry of the air. Certain instruments cannot tolerate water entering into the internal space because of their applications or characteristics and thus employ waterproofing measures, thereby becoming waterproof instruments. Accordingly, in an instrument that must be waterproof and allow air communication between the exterior thereof and the internal space, the air vent must also be waterproof and allow air communication.

An example of such a waterproof instrument is the oxygen sensor disclosed in Patent Document 1. The oxygen sensor has an oxygen detection element configured such that an internal electrode is formed on the inner surface of an axially extending tubular solid electrolyte element having a closed tip end and an open rear end, whereas an external electrode is formed on the outer surface of the solid electrolyte element. The air, which serves as a reference gas, is brought into contact with the inner surface of the solid electrolyte element, and an exhaust gas, which is a gas to be measured, is brought into contact with the outer surface of the solid electrolyte element. By utilizing electromotive force induced by an oxygen concentration cell effect between the internal and external electrodes, oxygen concentration is detected.

The oxygen sensor includes a metallic shell adapted to fix the oxygen detection element, and a sleeve portion whose tip end portion is fixedly attached to the rear end of the metallic shell and which extends axially in a direction opposite the metallic shell so as to cover a rear end portion of the oxygen detection element. A grommet having an air through-hole formed at its center is fit into the open end of the sleeve portion, and the sleeve portion and the grommet are airtightly sealed together. Accordingly, the internal electrode is accommodated in an internal space defined by the metallic shell, the sleeve portion, and the grommet. The air is introduced into the internal space through the air through-hole of the grommet.

If introduction of the air into the internal space of the oxygen detection element is accompanied by water, there is a risk of a short circuit occurring between metallic terminals connected to the internal and external electrodes of the oxygen detection element and a short circuit between the above-mentioned metallic terminals and metallic terminals for supply of electricity to a heater accommodated, together with the oxygen detection element, in the internal space. Such short circuit potentially results in a failure to properly detect electromotive force induced by the oxygen concentration cell effect.

In order to cope with this problem, the oxygen sensor can employ a resin sheet of a porous, fibrous structure having air permeability and water repellency. Specifically, the resin sheet is pressed into the air through-hole by use of an open-ended tubular metal member, thereby forming a water-repellent filter structure. The water-repellent filter structure prevents entry of water into the internal space from the exterior of the oxygen sensor while maintaining air communication through the air through-hole. By virtue of this structure, the oxygen sensor can have high reliability. Namely, while the internal electrode of the oxygen detection element is in contact with the air, no water enters the internal space thereof.

[Patent Document 1] Japanese Patent Application Laid-Open (kokai) No. 2000-193632 (FIGS. 1 and 3)

3. Problems to be Solved by the Invention

However, as mentioned above, when the resin sheet is pressed into the air through-hole using the tubular metal member so as to form the water-repellent filter structure, wrinkled portions of the resin sheet are present between the tubular metal member and the wall surface of the air through-hole.

Since any gap between the resin sheet and the wall surface of the air through-hole risks the entry of water therethrough, the outside diameter of the tubular metal member and the diameter of the air through-hole are rendered substantially equal to each other. Accordingly, when the resin sheet, together with the tubular metal member, are pressed into the air through-hole, friction arises on the resin sheet held between the internal tubular metal member and the air through-hole and generates high insertion resistance. The resin sheet is pressed into the air through-hole against the insertion resistance by inserting the tubular metal member.

Since the resin sheet and the tubular metal member are forcibly pressed into the through-hole, a large insertion force or load is applied to the resin sheet, particularly on a portion (shoulder portion) corresponding to an edge portion of the leading end of the tubular metal member. This involves the risk of cracking or breakage at the shoulder portion of the resin sheet, potentially resulting in impaired reliability and yield. Also, since application of a large load is required for insertion, it is not an easy task to form such a water-repellent filter structure.

SUMMARY OF THE INVENTION

The present invention has been accomplished in view of the above problems, and it is therefore an object of the invention to provide a water-repellent filter member whose handling is easy despite use of a resin sheet of a porous, fibrous structure having air permeability and water repellency, and a water-repellent filter member which allows easy insertion thereof into an air through-hole while avoiding cracking or breakage. Another object of the invention is to provide a method of manufacturing the water-repellent filter member. Still another object of the invention is to provide a waterproof instrument having air permeability and water repellency, and a gas sensor that serves as a waterproof instrument.

The above objectives of the invention have been achieved by providing (1) a water-repellent filter member formed from a resin sheet of a porous, fibrous structure having air permeability and water repellency, and comprising a tubular side wall portion and a bottom wall portion closing one end of the tubular side wall portion. At least a portion of the bottom wall portion maintains the porous, fibrous structure of the resin sheet and thereby has air permeability.

The water-repellent filter member of the present invention is formed by subjecting a resin sheet to forming work and has a tubular side wall portion and a bottom wall portion. As compared with use of a mere resin sheet, the water-repellent filter member can be handled more easily. Since the water-repellent filter member has a formed tubular side wall portion, even when the tubular side wall portion and the bottom wall portion, together with an internal tubular member, are to be inserted into an air through-hole of an enclosure member such as a grommet, the insertion work can be performed under a smaller load as compared with the conventional practice of using a resin sheet alone. Accordingly, the load imposed on a shoulder portion located between the bottom wall portion and the tubular side wall portion can be reduced, thereby preventing occurrence of cracking (breakage) in the shoulder portion. Since the bottom wall portion has air permeability, the bottom wall portion functions as a water-repellent filter. Therefore, the water-repellent filter member is easy to handle and can provide high reliability.

When the tubular side wall portion has sufficient rigidity, the following separate insertion tasks may be employed: the tubular side wall portion and the bottom wall portion of the water-repellent filter member are inserted into the air through-hole; and subsequently, an open-ended internal tubular member is inserted into the tubular side wall portion fitted into the air through-hole. This facilitates insertion of the tubular side wall portion and the bottom wall portion of the water-repellent filter member, since the internal tubular member is absent. Furthermore, since the internal tubular member can be inserted into the water-repellent filter member without imposing a load on the bottom wall portion and the shoulder portion, which readily break, a highly reliable water-repellent filter structure can be formed. Also, the water-repellent filter member can be used alone in the air through-hole without the internal tubular member.

Preferably, the water-repellent filter member further has a flange portion extending radially outward from an end of the tubular side wall portion opposite the bottom wall portion. When the tubular side wall portion and the bottom wall portion are inserted into the air through-hole, the flange portion can fix the depth of insertion.

The above objects of the invention are also achieved by providing (2) a water-repellent filter member comprising an internal tubular member having a tubular form and allowing air communication therethrough past a first end thereof and a second end thereof, and a closed-bottomed tubular resin member. The closed-bottomed tubular member is formed of a resin sheet of a porous, fibrous structure having air permeability and water repellency. As such, the resin member including a bottom wall portion closing the first end of the internal tubular member and a tubular side wall portion covering at least a portion of the outer circumferential surface of the internal tubular member (the portion being located adjacent to the first end of the internal tubular member), at least a portion of a bottom wall portion of the resin member (the bottom wall portion closing the first end of the internal tubular member) maintaining the porous, fibrous structure of the resin sheet and has air permeability.

The water-repellent filter member of the present invention assumes an integral form of the internal tubular member and the resin member, which is formed of a resin sheet of a porous, fibrous structure having air permeability and water repellency. Since at least a portion of the bottom wall portion of the resin member has air permeability, appropriate air communication can be established through the bottom wall portion.

Since the resin member and the internal tubular member are integrally formed, the resultant water-repellent filter member is easier to handle as compared with the case where two members; i.e., an internal tubular member and a water-repellent filter member formed of a resin sheet, are fitted into an air through-hole or the like.

The water-repellent filter member of the present invention assumes an integral form of the resin member and the internal tubular member. Accordingly, as compared with the above-mentioned case where the internal tubular member is inserted into the water-repellent filter member formed of the resin sheet, and a resultant assembly is inserted into the air through-hole, resistance force induced by friction associated with insertion can also be dispersed to the internal tubular member. This reduces stress that is induced by insertion resistance associated with insertion into the air through-hole and is imposed on the bottom wall portion and the shoulder portion of the resin member, thereby preventing occurrence of cracking or the like in the bottom and shoulder portions.

No particular limitation is imposed on the internal tubular member, so long as the internal tubular member is resistant to heat that is applied in the course of forming the resin member from a resin sheet. Material for the internal tubular member may be selected in view of environmental conditions and the like involved in use. Specific examples of the material include metal materials, such as stainless steel and aluminum; ceramics such as alumina; glass; and heat-resistant resin materials such as PTFE and polyimide.

No particular limitation is imposed on the internal tubular member, so long as the internal tubular member allows air communication therethrough past one end thereof and the other end thereof. Specifically, the internal tubular member may assume a tubular form whose opposite ends are open or whose one end or opposite ends each have an internal flange extending radially inward.

Preferably, in the above-mentioned water-repellent filter member, (3) the internal tubular member has an engagement portion formed on the outer circumferential surface thereof and adapted to engage with the resin member so as to prevent detachment of the resin member.

In the water-repellent filter member of the present invention, the internal tubular member has an engagement portion formed on the outer circumferential surface thereof and is adapted to engage with the resin member; thus, the resin member does not detach from the internal tubular member. As compared with the case where the engagement portion is not formed, when the water-repellent filter member is inserted into a through-hole of a grommet, insertion resistance can be more reliably dispersed to the internal tubular member, so that stress is less likely to be imposed on the bottom wall portion and the shoulder portion of the resin member. Thus, the present invention provides a water-repellent filter member in which cracking or the like is unlikely to occur and which provides high reliability.

No particular limitation is imposed on the engagement portion, so long as the engagement portion assumes such form so as to exhibit sufficient engaging force to prevent detachment of the resin member formed integrally with the outer circumferential surface of the internal tubular member. The engagement portion may assume a form such that, even when insertion resistance is imposed on an assembly of the resin member and the internal tubular member in the course of inserting the assembly into an air through-hole, the engagement portion exhibits sufficient engaging force to maintain the integrated condition of the resin member and the internal tubular member. Specific examples of the form include pits and projections formed on the outer circumferential surface of the internal tubular member by blasting, knurling, or the like; and a through-hole extending through the internal tubular member between the outer circumferential surface and the inner circumferential surface.

The above objects of the invention are also achieved by providing (4) a method of manufacturing a water-repellent filter member formed from a resin sheet of a porous, fibrous structure having air permeability and water. The water-repellent filter member comprises a tubular side wall portion, and a bottom wall portion closing one end of the tubular side wall portion, at least a portion of the bottom wall portion maintaining the porous, fibrous structure of the resin sheet and thereby having air permeability. The manufacturing method comprises covering a tip end of a rodlike portion of a male die member and a radially outer circumferential surface of the rodlike portion with the resin sheet; and heating the resin sheet while maintaining at least a portion of a sheet projectional-end portion of the resin sheet located axially outside of the tip end of the rodlike portion at such a temperature as not to cause mutual fusion of fibers of the porous, fibrous structure and then solidifying at least a base-end-side circumferential portion of the resin sheet located radially outward of a base-end-side portion of the rodlike portion located away from the tip end of the rodlike portion, so as to form the tubular side wall portion and the bottom wall portion.

The method of manufacturing a water-repellent filter member of the present invention employs a male die member having a rodlike portion. At least a portion of the resin sheet located radially outward of a base-end-side portion of the rodlike portion located away from the tip end of the rodlike portion is heated and solidified, thereby forming the tubular side wall portion. Also, at least a portion of a sheet projectional-end portion (which will become the bottom wall portion of the water-repellent filter member) of the resin sheet located axially outside of the tip end of the rodlike portion of the male die member is maintained at such a temperature as not to cause mutual fusion of fibers of the porous, fibrous structure.

Accordingly, the tubular side wall portion can be formed from a resin sheet, and, even after forming work, at least a portion of the sheet projectional-end portion of the resin sheet can retain the porous, fibrous structure of the original resin sheet. The manufacturing method, therefore, can reliably manufacture a water-repellent filter member that has the tubular side wall portion and in which at least a portion of the bottom wall portion retains the porous, fibrous structure of the resin sheet and thus has air permeability.

Preferably, the tubular side wall portion (or a portion of the resin sheet that will become the tubular side wall portion) is heated from a radially outside direction. However, the present invention is not limited thereto. For example, the tubular side wall portion may be heated from a radially inside direction by increasing the temperature of the rodlike portion of the male die member while avoiding mutual fusion of the fibers of the porous, fibrous structure of the sheet projectional-end portion (a portion corresponding to the bottom wall portion) covering the tip end of the rodlike portion of the male die member so as to prevent loss of air permeability.

Preferably, in the above-mentioned method of manufacturing a water-repellent filter member, (5) heat is applied to the base-end-side circumferential portion of the resin sheet while the base-end-side circumferential portion of the resin sheet is pressed against the outer circumferential surface of the rodlike portion from a radially outside direction.

In the method of manufacturing a water-repellent filter member of the present invention, the base-end-side circumferential portion of the resin sheet is heated and pressed against the outer circumferential surface of the rodlike portion from a radially outside direction. Accordingly, the profile of a portion of the tubular side wall portion of the formed water-repellent filter member that corresponds to the base-end-side circumferential portion is not influenced by wrinkled portions of the resin sheet appearing during the course of forming, and undergoes forming while being profiled with a pressing die. Therefore, the method of manufacturing a water-repellent filter member of the present invention is capable of reliably forming a water-repellent filter member having a predetermined profile.

By means of imparting a predetermined outside diameter to the water-repellent filter member, the tubular side wall portion of the water-repellent filter member can be readily inserted into an air through-hole under a small load; in other words, the manufacturing method can provide a water-repellent filter member that can be handled easily.

Preferably, in the above-mentioned method of manufacturing a water-repellent filter member according to (4) or (5) above, (6) the rodlike portion of the male die member assumes a tubular form having an open tip end or has on its tip end face a recess opening toward its tip end. Also, the bottom wall portion is formed while at least a portion, or a noncontact portion, of the sheet projectional-end portion of the resin sheet is maintained out of contact with the rodlike portion of the male die member so as to be held at such a temperature as not to cause mutual fusion of the porous, fibrous structure.

Conceivably, a male die member having a rodlike portion for use in manufacture of a water-repellent filter member is configured such that the rodlike portion is solid and has no recess formed on its tip end face. Use of a male die member having such a rodlike portion involves the risk of mutual fusion of the fibers of the porous, fibrous structure. This is the result of transmission of heat from the rodlike portion to the sheet projectional-end portion of the resin sheet and an associated increase in temperature of the sheet projectional-end portion.

By contrast, the method of manufacturing a water-repellent filter member of the present invention uses a rodlike portion that assumes a tubular form or has a recess formed on its tip end face. By virtue of the use of such a rodlike portion, at least a portion of the sheet projectional-end portion of the resin sheet becomes a noncontact portion that is separate from the rodlike portion (a tip end portion of the rodlike portion). Since heat is not directly transmitted from the rodlike portion to the noncontact portion, the noncontact portion can be maintained at such a low temperature as not to cause mutual fusion of the fibers. Thus, the noncontact portion is free from mutual fusion of the fibers. Since at least a portion of the bottom wall portion of the formed water-repellent filter member can maintain the porous, fibrous structure of the resin sheet, the portion can have air permeability.

Accordingly, the method of manufacturing a water-repellent filter member of the present invention can reliably provide a water-repellent filter member that has air permeability at the bottom wall portion thereof.

Preferably, in the above-mentioned method of manufacturing a water-repellent filter member according to any one of (4) to (6) above, (7) the bottom wall portion is formed while at least a portion, or an abutment portion, of the sheet projectional-end portion of the resin sheet is brought into contact with a heat release member from axially outside the tip end of the rodlike portion of the male die member so as to be held at such a temperature as not to cause mutual fusion of the fibers.

In manufacture of a water-repellent filter member, use of a male die member having a rodlike portion involved the risk of mutual fusion of fibers of the porous, fibrous structure as a result of transmission of heat from the rodlike portion to the sheet projectional-end portion of the resin sheet and an associated increase in temperature of the sheet projectional-end portion.

By contrast, the manufacturing method of the present invention uses the heat release member in such manner that at least a portion, or an abutment portion, of the sheet projectional-end portion of the resin sheet is brought into contact with the heat release member so as to be held at such a low temperature as not to cause fusion of the fibers.

Accordingly, the abutment portion is free from fusion of the fibers. After the water-repellent filter member is formed, at least a portion of the bottom wall portion thereof maintains the porous, fibrous structure and thus has air permeability. Thus, the method of manufacturing a water-repellent filter member of the present invention can reliably provide a water-repellent filter member that has air permeability at the bottom wall portion thereof.

Preferably, the abutment portion also assumes the form of the noncontact portion. Specifically, the rodlike portion assumes a tubular form or has a recess formed on its tip end face, so that the abutment portion (noncontact portion) comes into contact with the heat release member, but does not come into contact with the rodlike portion. This more reliably prevents an increase in temperature of the abutment portion.

Preferably, in the above-mentioned method of manufacturing a water-repellent filter member according to any one of (4) to (6) above, (8) the bottom wall portion is formed while at least a portion, or a portion-to-be-cooled, of the sheet projectional-end portion of the resin sheet is brought into contact with fluid having a temperature lower than the melting temperature of the resin sheet from axially outside the tip end of the rodlike portion of the male die member so as to be held at such a temperature as not to cause mutual fusion of the fibers.

In manufacture of a water-repellent filter member, use of a male die member having a rodlike portion involved the risk of mutual fusion of fibers of the porous, fibrous structure as a result of transmission of heat from the rodlike portion to the sheet projectional-end portion of the resin sheet and an associated increase in temperature of the sheet projectional-end portion.

By contrast, the manufacturing method of the present invention uses a fluid in such manner that at least a portion, or a portion-to-be-cooled, of the sheet projectional-end portion of the resin sheet is cooled by the fluid so as to be held at such a low temperature as not to cause fusion of the fibers.

Accordingly, the portion-to-be-cooled is free from fusion of the fibers, which could otherwise result from transmission of heat from the rodlike portion. After the water-repellent filter member is formed, at least a portion of the bottom wall portion thereof maintains the porous, fibrous structure and thus has air permeability. Thus, the method of manufacturing a water-repellent filter member of the present invention can reliably provide a water-repellent filter member that has air permeability at the bottom wall portion thereof.

Example methods of bringing a fluid into contact with a portion-to-be-cooled include a method of blowing gas such as cold air onto the portion-to-be-cooled, a method of bringing liquid such as water into contact with the portion-to-be-cooled, and a method of exposing the portion-to-be-cooled to flowing liquid such as flowing water.

Preferably, the portion-to-be-cooled also assumes the form of the noncontact portion. Specifically, the rodlike portion assumes a tubular form or has a recess formed on its tip end face, so that the portion-to-be-cooled (noncontact portion) is cooled by fluid and does not come into contact with the rodlike portion. This more reliably prevents an increase in temperature of the portion-to-be-cooled.

The above objects of the invention are also achieved by providing (9) a method of manufacturing a water-repellent filter member that comprises an internal tubular member having a tubular form and allowing air communication therethrough past a first end thereof and a second end thereof, and a closed-bottomed tubular resin member. The closed-bottomed tubular resin member is formed of a resin sheet of a porous, fibrous structure having air permeability and water repellency, by subjecting the internal tubular member and the resin sheet to integral forming such that the resin sheet covers the first end of the internal tubular member and at least a portion of the outer circumferential surface of the internal tubular member, the portion being located adjacent to the first end of the internal tubular member, so as to close the first end of the internal tubular member. At least a portion of a bottom wall portion of the resin member, the bottom wall portion closing the first end of the internal tubular member, maintains the porous, fibrous structure of the resin sheet and has air permeability. The manufacturing method comprises covering the internal tubular member with the resin sheet at least in such manner as to close the first end of the internal tubular member and to cover the outer circumferential surface of the internal tubular member; forming the bottom wall portion while maintaining at least a portion of a first-end-closing portion of the resin sheet located axially outside the first end of the internal tubular member at such a temperature as not to cause mutual fusion of fibers of the porous, fibrous structure; and heating and then solidifying an exterior-of-tubular-member portion of the resin sheet located radially outward of the internal tubular member so as to integrate the resin member with the internal tubular member.

In the method of manufacturing a water-repellent filter member of the present invention, when the internal tubular member and the resin sheet covering the internal tubular member are subjected to integral forming so as to integrate the resin member with the internal tubular member, a portion of the first-end-closing portion of the resin sheet is held at a temperature not higher than the fusion temperature of the fibers.

Accordingly, at least a portion of the first-end-closing portion is free from mutual fusion of the fibers. After the water-repellent filter member is formed, at least a portion of the bottom wall portion thereof maintains the porous, fibrous structure of the resin sheet and thus has air permeability. Thus, the method of manufacturing a water-repellent filter member of the present invention can reliably provide a water-repellent filter member that has air permeability at the bottom wall portion thereof.

The present invention also provides a waterproof instrument (10) having an internal space in air communication with the exterior thereof and comprising a waterproof enclosure member, enclosing at least a portion of the internal space, and having an air through-hole extending therethrough and establishing air communication between the internal space and the exterior of the waterproof instrument, and a water-repellent filter member fitted into the air through-hole of the enclosure member, allowing air communication between the internal space and the exterior of the waterproof instrument through the air through-hole, and preventing entry of water into the internal space through the air through-hole. In the waterproof instrument, the water-repellent filter member is that according to any one of (1) to (3) above.

The waterproof instrument of the present invention allows air communication between the internal space and the exterior thereof through the air through-hole of the enclosure member. The water-repellent filter member according to any one of (1) to (3) above is fitted into the air through-hole. Since, in the course of being fitted into the air through-hole, the water-repellent filter member according to any one of (1) to (3) above does not suffer cracking (breakage) in the bottom wall portion and the shoulder portion, the waterproof instrument of the present invention is highly reliable.

The above objects of the invention have also been achieved by providing (11) a method of manufacturing a waterproof instrument having an internal space in air communication with the exterior thereof. The waterproof instrument comprises a waterproof enclosure member, enclosing at least a portion of the internal space, and having an air through-hole extending therethrough and establishing air communication between the internal space and the exterior of the waterproof instrument, and a water-repellent filter member fitted into the air through-hole of the enclosure member, allowing air communication between the internal space and the exterior of the waterproof instrument through the air through-hole, and preventing entry of water into the internal space through the air through-hole. The water-repellent filter member is formed of a water-repellent material and comprises an axially extending tubular side wall portion, and a bottom wall portion closing one end of the tubular side wall portion. At least a portion of the bottom wall portion maintains the porous, fibrous structure of the resin sheet and thereby has air permeability. The manufacturing method includes a filter-attaching process that comprises inserting the bottom wall portion and at least a portion of the tubular side wall portion of the water-repellent filter member into the air through-hole of the enclosure member, and inserting an internal tubular member having a tubular form and allowing air communication therethrough past a first end thereof and a second end thereof into the tubular side wall portion of the water-repellent filter member fitted into the air through-hole so as to press-fit at least a portion of the tubular side wall portion of the water-repellent filter member against the wall of the air through-hole, thereby attaching the water-repellent filter member into the air through-hole.

According to the filter-attaching process of the method of manufacturing a waterproof instrument, first, the water-repellent filter member is inserted into the air through-hole of the enclosure member; and subsequently, the internal tubular member is inserted into the tubular side wall portion of the water-repellent filter member that has already been inserted into the air through-hole. As compared with the case where the internal tubular member and the water-repellent filter member covering the internal tubular member are inserted in unison into the air through-hole of the enclosure member, the water-repellent filter member can be inserted into the air through-hole with smaller force. This is because, when the water-repellent filter member is inserted into the air through-hole, only the bottom wall portion and the tubular side wall portion thereof are inserted, so that the insertion work is facilitated. In inserting the internal tubular member, the internal tubular member may be inserted in sliding relation with the tubular side wall portion of the water-repellent filter member. This facilitates the attachment work for the internal tubular member, since the pressing force required for insertion is smaller as compared with the case of joint insertion of the internal tubular member and the water-repellent filter member. Furthermore, in the course of inserting the internal tubular member, little stress is imposed on the bottom wall portion and the shoulder portion of the previously inserted water-repellent filter member. Therefore, deformation or breakage, such as cracking, of the water-repellent filter member can be reliably prevented.

No particular limitation is imposed on inserting the water-repellent filter member in the method of manufacturing a waterproof instrument, so long as the water-repellent filter member is inserted into the air through-hole of the enclosure member. Specifically, a water-repellent filter (the bottom wall portion and the entire tubular side wall portion) is not necessarily disposed within the air through-hole. For example, the bottom wall portion of the water-repellent filter member may be located within the air through-hole or ahead of the air through-hole with respect to the insertion direction. The tubular side wall portion of the water-repellent filter member may be entirely disposed within the air through-hole, or a portion (a portion of the tubular side wall portion located in the vicinity of the bottom wall portion) of the tubular side wall portion may extend beyond the air through-hole with respect to the insertion direction. The remaining portion (a base-end portion opposite the bottom wall portion) of the tubular side wall portion of the water-repellent filter member may be located behind the air through-hole of the enclosure member with respect to the insertion direction; i.e., not inserted into the air through-hole.

No particular limitation is imposed on inserting the water-repellent filter member in the method of manufacturing a waterproof instrument, so long as at least a portion of the bottom wall portion thereof has a predetermined air permeability. For example, the water-repellent filter member may be configured such that separate members serving as the bottom wall portion and the tubular side wall portion are bonded together.

The present invention further provides (12) a gas sensor comprising a gas detection element in contact with a reference gas via a first surface and in contact with a gas to be measured via a second surface opposite the first surface, and a waterproof enclosure member defining, together with the gas detection element, an internal space to which the first surface of the gas detection element is exposed but the second surface of the gas detection element is not exposed. In the gas sensor, the enclosure member includes a waterproof grommet, enclosing at least a portion of the internal space, having an air through-hole extending therethrough, establishing air communication between the internal space and the exterior of the gas sensor, and formed of a rubberlike elastic material; the grommet has a water-repellent filter member fitted into the air through-hole thereof, allowing air communication between the internal space and the exterior of the gas sensor through the air through-hole, and preventing entry of water into the internal space through the air through-hole; and the water-repellent filter member is one according to any one of (1) to (3) above.

The gas sensor of the present invention allows air communication between the internal space and the exterior thereof through the air through-hole of the grommet. The water-repellent filter member according to any one of (1) to (3) above is fitted into the air through-hole. Since, in the course of being fitted into the air through-hole, the water-repellent filter member according to any one of (1) to (3) above does not suffer cracking (breakage) in the bottom wall portion and the shoulder portion, the gas sensor of the present invention is highly reliable.

The above objects of the invention are also achieved by providing (13) a method of manufacturing a gas sensor comprising a gas detection element in contact with a reference gas via a first surface and in contact with a gas to be measured via a second surface opposite the first surface, and a waterproof enclosure member defining, together with the gas detection element, an internal space to which the first surface of the gas detection element is exposed but the second surface of the gas detection element is not exposed. In the gas sensor, the enclosure member includes a waterproof grommet, enclosing at least a portion of the internal space, having an air through-hole extending therethrough, establishing air communication between the internal space and the exterior of the gas sensor, and formed of a rubberlike elastic material; and the grommet has a water-repellent filter member fitted into the air through-hole thereof, allowing air communication between the internal space and the exterior of the gas sensor through the air through-hole, and preventing entry of water into the internal space through the air through-hole. The water-repellent filter member is formed of a water-repellent material and comprises an axially extending tubular side wall portion, and a bottom wall portion closing one end of the tubular side wall portion. At least a portion of the bottom wall portion maintains the porous, fibrous structure and thereby has air permeability. The manufacturing method includes a filter-attaching process that comprises inserting the bottom wall portion and at least a portion of the tubular side wall portion of the water-repellent filter member into the air through-hole of the grommet, and inserting an internal tubular member having a tubular form and allowing air communication therethrough past a first end thereof and a second end thereof into the tubular side wall portion of the water-repellent filter member fitted into the air through-hole so as to press-fit at least a portion of the tubular side wall portion of the water-repellent filter member against the wall of the air through-hole, thereby attaching the water-repellent filter member into the air through-hole.

According to the filter-attaching process of the method of manufacturing a gas sensor, first, the water-repellent filter member is inserted into the air through-hole of the grommet; and subsequently, the internal tubular member is inserted into the tubular side wall portion of the water-repellent filter member that has already been inserted into the air through-hole. As compared with the case where the internal tubular member and the water-repellent filter member covering the internal tubular member are inserted in unison into the air through-hole of the grommet, the water-repellent filter member can be inserted into the air through-hole with smaller force. This is because, when the water-repellent filter member is inserted into the air through-hole, only the bottom wall portion and the tubular side wall portion thereof are inserted, so that the insertion work is facilitated. In inserting the internal tubular member, the internal tubular member may be inserted in sliding relation with the tubular side wall portion of the water-repellent filter member. This facilitates the attachment work for the internal tubular member, since the pressing force required for insertion is smaller as compared with the case of joint insertion of the internal tubular member and the water-repellent filter member. Furthermore, in the course of inserting the internal tubular member, little stress is imposed on the bottom wall portion and the shoulder portion of the water-repellent filter member. Therefore, deformation or breakage, such as cracking, of the water-repellent filter member can be reliably prevented.

No particular limitation is imposed on inserting the water-repellent filter member in the method of manufacturing a gas sensor, so long as the water-repellent filter member is inserted into the air through-hole of the grommet. Specifically, a water-repellent filter (the bottom wall portion and the entire tubular side wall portion) is not necessarily disposed within the air through-hole. For example, the bottom wall portion of the water-repellent filter member may be located within the air through-hole or ahead of the air through-hole with respect to the insertion direction. The tubular side wall portion of the water-repellent filter member may be entirely disposed within the air through-hole, or a portion (a portion of the tubular side wall portion located in the vicinity of the bottom wall portion) of the tubular side wall portion may extend beyond the air through-hole with respect to the insertion direction. The remaining portion (a base-end portion opposite the bottom wall portion) of the tubular side wall portion of the water-repellent filter member may be located behind the air through-hole of the enclosure member with respect to the insertion direction; i.e., not inserted into the air through-hole.

BRIEF DESCRIPTION OF THE DRAWINGS

FIGS. 6(a) and 6(b) are electron micrographs showing structures of the water-repellent filter member according to Embodiment 1, wherein FIG. 6(a) shows a bottom wall portion, and FIG. 6(b) shows a tubular side wall portion.

FIGS. 7(a) and 7(b) are explanatory views showing a method of manufacturing a water-repellent filter member according to Embodiment 1, wherein FIG. 7(a) shows a state before forming, and FIG. 7(b) shows a state in the midst of forming.

FIGS. 8(a) to 8(c) are explanatory views showing a method of manufacturing a water-repellent filter member according to Modified Embodiment 1 of the invention, wherein FIG. 8(a) shows a state before forming; FIG. 8(b) shows a state in which a resin sheet is pressed into a forming hole of a female die member by means of a rodlike portion of a male die member; and FIG. 8(c) shows a state of thermoforming a tubular side wall portion.

FIGS. 9(a) and 9(b) are explanatory views showing a method of manufacturing a water-repellent filter member according to Modified Embodiment 2 of the invention, wherein FIG. 9(a) shows a state before forming, and FIG. 9(b) shows a state in the midst of forming.

FIGS. 13(a) to 13(c) are explanatory views showing a method of manufacturing a water-repellent filter member according to Embodiment 2 of the invention, wherein FIG. 13(a) shows a state before forming; FIG. 13(b) shows a state in which a resin sheet is pressed into a forming hole of a female die member by means of an internal tubular member; and FIG. 13(c) shows a state of thermoforming a tubular side wall portion.

DESCRIPTION OF REFERENCE NUMERALS

Figure 1:
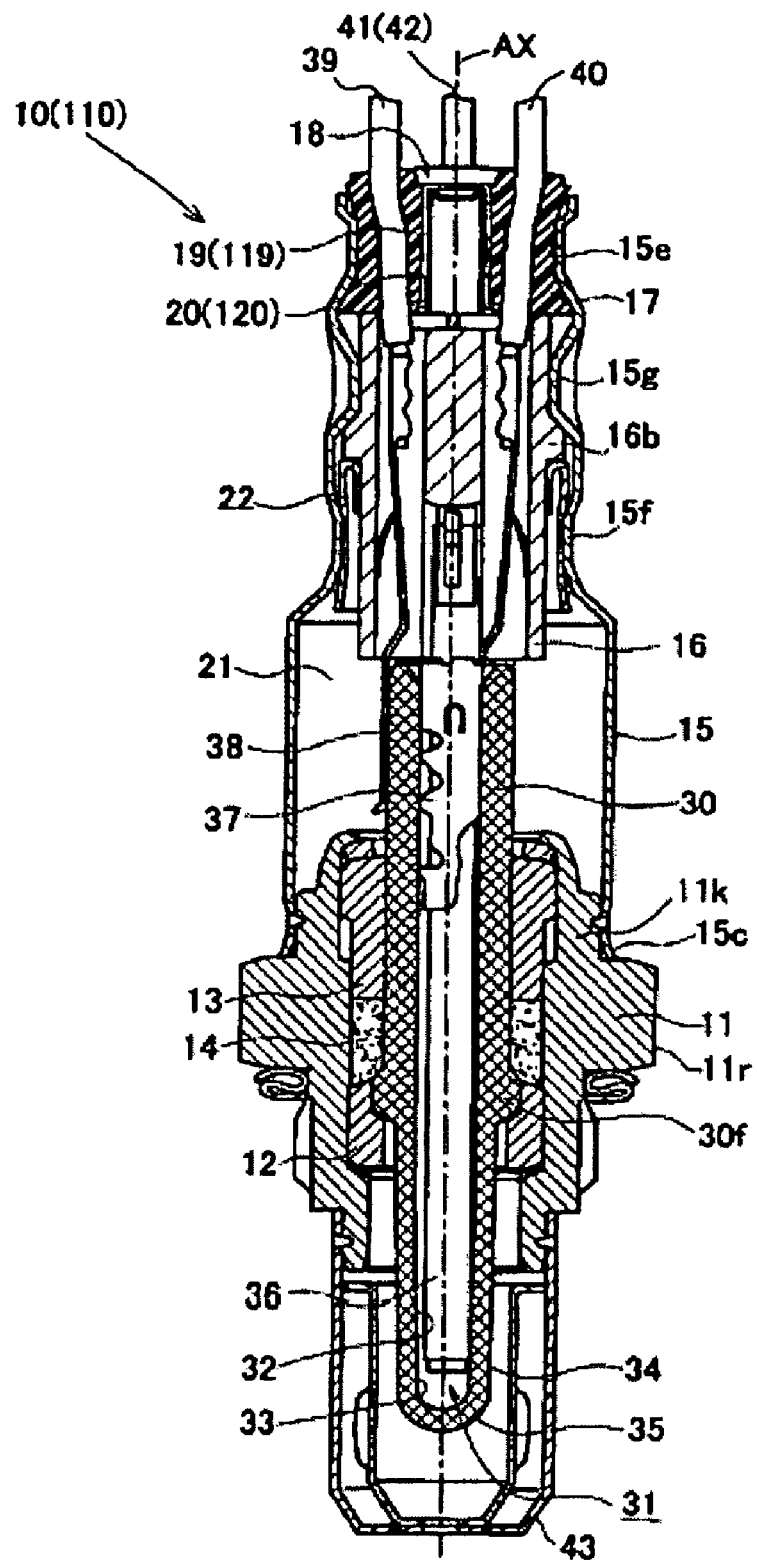
FIG. 1 is a vertical sectional view showing an oxygen sensor according to Embodiment 1 of the invention.

Reference numerals used to identify various structural features in the drawings include the following.
10, 110: oxygen sensor
15: metallic sleeve (enclosure member)
17: grommet (enclosure member)
18: air through-hole (of grommet)
19: water-repellent filter member
200: water-repellent filter member
119: resin member
119c: engagement portion (of resin member)
20, 120: internal tubular member 120c: through-hole (engagement portion) (of internal tubular member)
21: internal space
30: oxygen detection element
32: inner surface (first surface)
34: outer surface (second surface)
50, 60, 70, 80: manufacturing apparatus for manufacturing water-repellent filter member
52, 62, 72: male die member
52b, 62b, 72b: rodlike portion (of male die member)
52g, 62g, 72g, 82g: outer circumferential surface (of rodlike portion)
52h, 62h, 72h: body portion (of male die member)
52k, 62k, 72k: base-end-side portion (of rodlike portion)
52s, 62s, 72s, 82s: tip end (of rodlike portion)
52t, 62t: hollow portion
52tk: opening (of hollow portion)
54, 64, 74, 84: resin sheet
54g, 64g, 74g: base-end-side circumferential portion (of resin sheet)
54r, 64r, 74r, 84r: noncontact portion (of resin sheet)
54s, 64s, 74s: sheet projectional-end portion (of resin sheet)
73: heat release member
73s: abutment face (of heat release member)
74t: abutment portion (of resin sheet)
82: tube rest
82b: fixing portion (of tube rest)
82h: body portion (of tube rest)
84g: base-end-side circumferential portion (of resin sheet)
84k: aperture-closing portion (first-end-closing portion) (of resin sheet)
AR: air

DETAILED DESCRIPTION OF THE PREFERRED EMBODIMENTS

Preferred embodiments of an oxygen sensor and a water-repellent filter member according to the present invention will now be described with reference to FIGS. 1 to 13. However, the present invention should not be construed as being limited thereto.

Embodiment 1

FIG. 1 is a vertical sectional view showing the internal structure of an oxygen sensor 10 according to Embodiment 1. The oxygen sensor 10 includes a closed-bottomed tubular oxygen detection element 30. The oxygen detection element 30 is closed at its tip end (the bottom in FIG. 1) and open at its rear end (the top in FIG. 1) and extends axially (in the vertical direction in FIG. 1) along an axis AX.

The oxygen detection element 30 is formed of an oxygen-ion-conductive solid electrolyte. A porous internal electrode 33 is formed of, for example, Pt or a Pt alloy and covers substantially the entire inner surface 32 of a closed-bottomed bore 31 of the oxygen detection element 30. The internal electrode 33 is in contact with an internal-electrode terminal member 37 and thereby electrically communicates with the internal-electrode terminal member 37. The electrical potential of the internal electrode 33 of the oxygen detection element 30 is externally output through a sensor output lead wire 40 connected to the internal-electrode terminal member 37.

A porous external electrode 35 similar to the internal electrode 33 is formed on a tip end portion of an outer surface 34 of the oxygen detection element 30. An external-electrode terminal member 38 is in contact with an external lead portion (unillustrated) formed on the outer surface 34 of the oxygen detection electrode 30 and extending rearward from the external electrode 35 and thereby electrically communicates with the external electrode 35. The electrical potential of the external electrode 35 of the oxygen detection element 30 is externally output through another sensor output lead wire 39 connected to the external-electrode terminal member 38.

A protector 43 is attached to a metallic shell 11 and covers a tip end portion of the oxygen detection element 30 that projects from a tip-end opening portion of the metallic shell 11. A plurality of gas transmission holes are formed in the protector 43 for allowing exhaust gas to pass therethrough. Accordingly, the external electrode 35 of the oxygen detection element 30 can come into contact with exhaust gas (gas to be measured) via the gas transmission holes of the protector 43.

An engagement flange portion 30f projecting radially outward is provided at an axially intermediate portion of the oxygen detection element 30. The metallic shell 11 is engaged with and holds, within its tubular interior, the engagement flange portion 30f via insulators 12 and 13 and a ceramic powder 14. A tip end portion 15c of a tubular metallic sleeve 15 is externally fixed, by crimping and laser welding, to a rear-end connection portion 11k located rearward of a hexagonal portion 11r. A grommet 17 formed of fluorine-containing rubber is fitted into a grommet crimp portion 15e located at the rear end of the metallic sleeve 15, and then the grommet crimp portion 15e is sealingly crimped. A separator 16 formed of insulating alumina ceramic is provided on the tip-end side of the grommet 17. The sensor output lead wires 39 and 40 and heater lead wires 41 and 42 extend through the grommet 17 and the separator 16.

Figure 2:
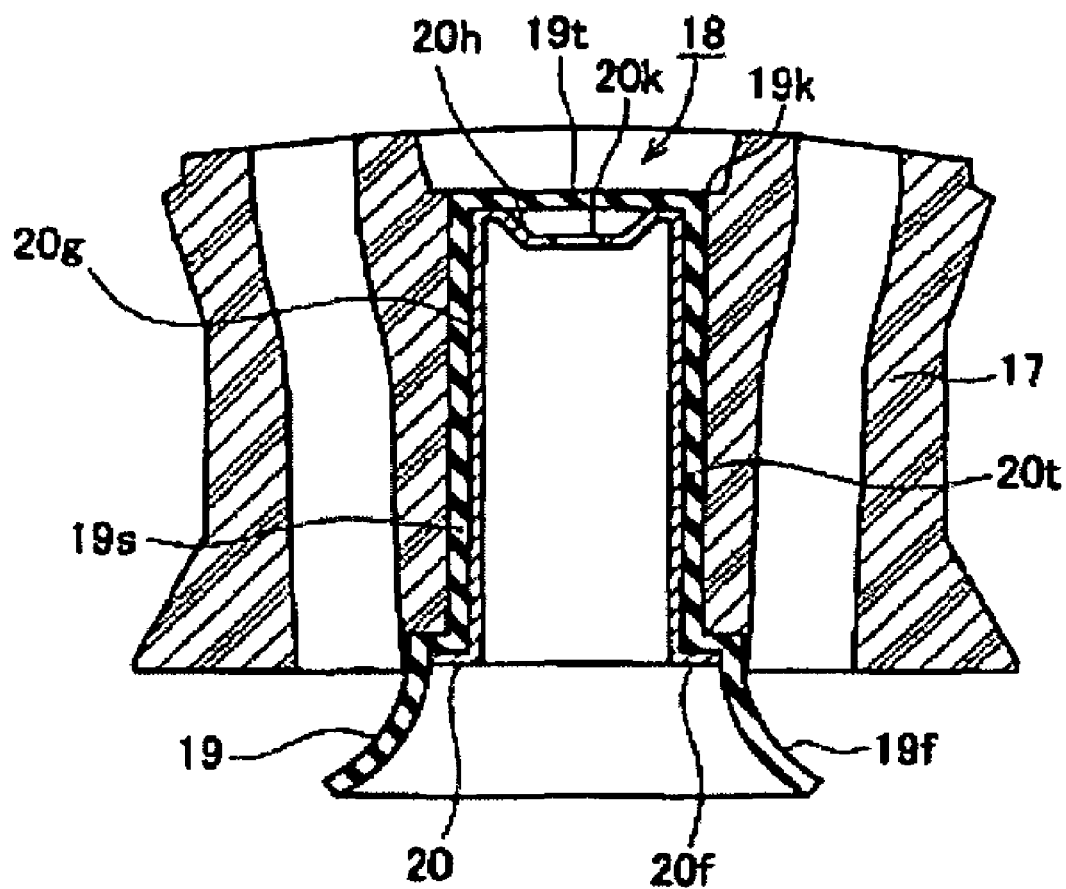
FIG. 2 is a vertical sectional view showing an assembled state of a grommet, an internal tubular member, and a water-repellent filter member of the oxygen sensor according to Embodiment 1.
Figure 3:
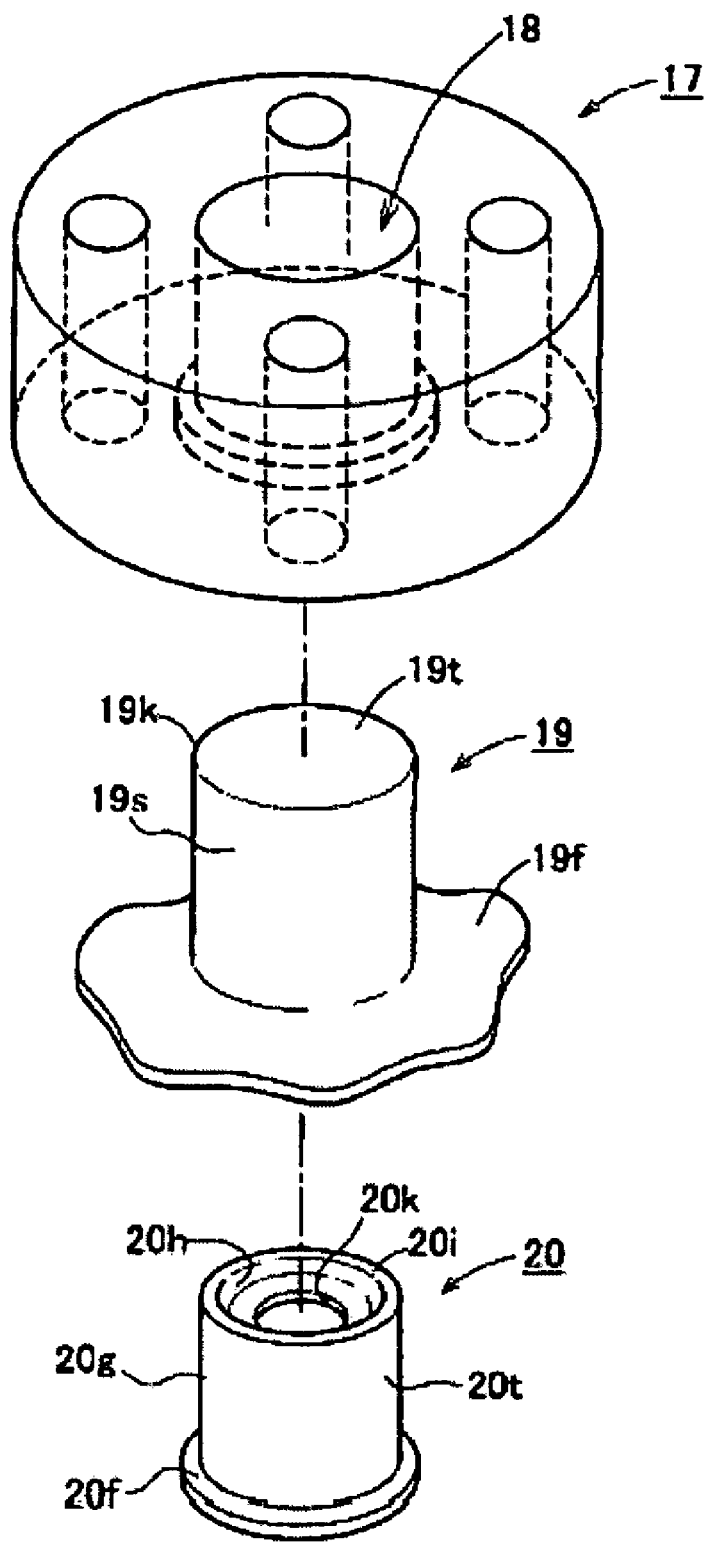
FIG. 3 is an exploded perspective view showing attachment of the internal tubular member and the water-repellent filter member to the grommet in Embodiment 1.

As shown in FIGS. 2 and 3, in addition to through-holes for the lead wires 39, 40, 41, and 42, an air through-hole 18 is formed at the center of the grommet 17 for the purpose of allowing air communication with the ambient air. A water-repellent filter member 19 having a shape resembling a top hat is fitted into the air through-hole 18. As a result of the grommet 17 being subjected to crimping, the water-repellent filter member 19 is held between the grommet 17 and an internal tubular member 20. Specifically, as a result of the diameter of the grommet 17 being reduced, a tubular side wall portion 19s of the water-repellent filter member 19 is pressed against an outer circumferential surface 20g of the internal tubular member 20, whereby the water-repellent filter member 19 is fixed in place.

Figure 5:
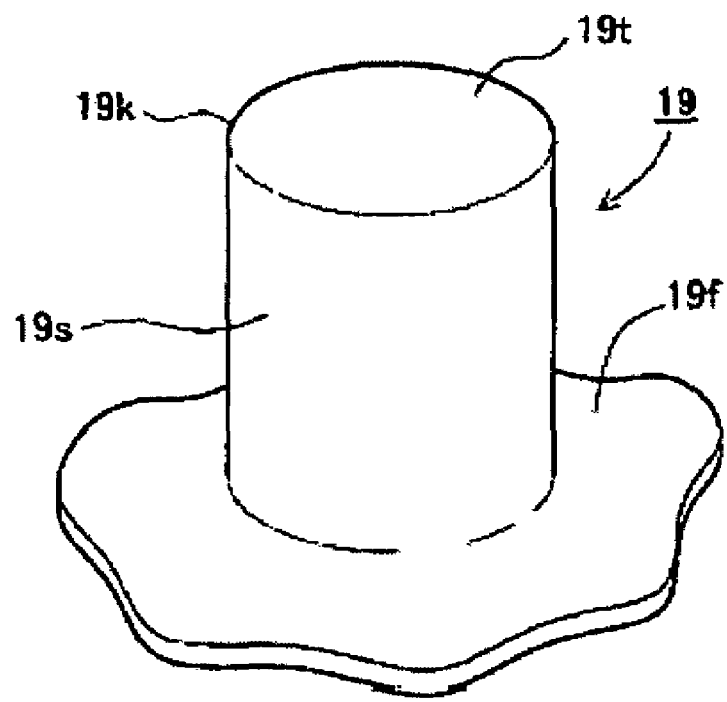
FIG. 5 is a perspective view of the water-repellent filter member according to Embodiment 1.

The water-repellent filter member 19 will be described in detail with reference to FIG. 5. The water-repellent filter member 19 is formed into a closed-bottomed cylindrical shape and includes an axially extending tubular side wall portion 19s having a cylindrical shape and a disklike bottom wall portion 19t that closes one end of the tubular side wall portion 19s. The water-repellent filter member 19 further includes a flange portion 19f extending radially outward from an end of the tubular side wall portion 19s opposite the bottom wall portion 19t. As will be described later, the water-repellent filter member 19 is formed by means of forming a resin sheet 54 of a porous, fibrous structure having air permeability and water repellency into a shape resembling a top hat (a closed-bottomed cylinder having a flange) (see FIGS. 7(a) and 7(b)). Since the bottom wall portion 19t is formed so as to hold the porous, fibrous structure of the resin sheet 54 (see FIG. 6(a)), the water-repellent filter member 19 functions as a water-repellent filter having air permeability at the bottom wall portion 19t.

Figure 4:
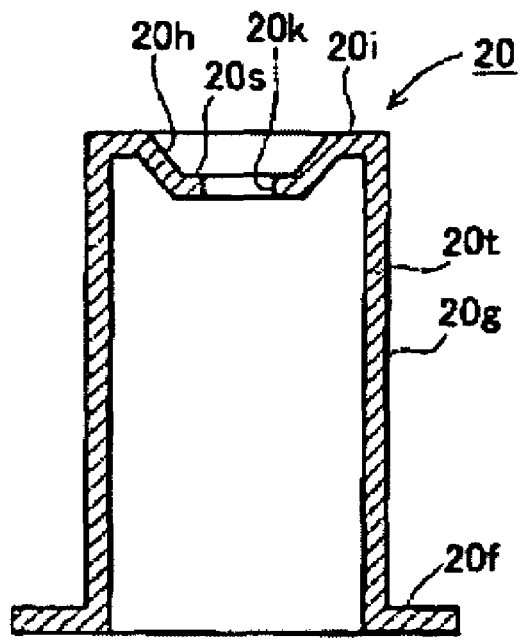
FIG. 4 is a vertical sectional view of the internal tubular member according to Embodiment 1.

Next, the internal tubular member 20 will be described. The internal tubular member 20 is formed of stainless steel and, as shown in FIG. 4, assumes a shape resembling a top hat.

The internal tubular member 20 has a tubular portion 20t. The tubular portion 20t has an internal flange portion 20h extending radially inward at a first axial end (the top in FIG. 4) 20i. The internal flange portion 20h has a first-end-side opening portion 20k at its center portion 20s. Accordingly, the internal tubular member 20 has a tubular form and allows air communication therethrough past the first end thereof and the second end thereof. In the internal tubular member 20 of Embodiment 1, the internal flange portion 20h is depressed toward the second axial end (the bottom in FIG. 4) with respect to the first end 20i, so that the first-end-side opening portion 20k is biased from the first end 20i toward the second axial end (the bottom in FIG. 4). The internal tubular member 20 has a flat, annular flange portion 20f projecting radially outward from the second end (the bottom in FIG. 4) of the tubular portion 20t.

As shown in FIG. 1, the oxygen sensor 10 has an internal space 21 defined by a surface of the oxygen detection element 30 including the inner surface 32, the metallic shell 11, the metallic sleeve 15, and the grommet 17. The water-repellent filter member 19 fitted into the air through-hole 18 of the grommet 17 allows the internal space 21 to aerially communicate with the ambient air and prevents entry of water into the internal space 21 through the air through-hole 18. Accordingly, by preventing entry of water into the internal space 21 of the oxygen sensor 10, the inner surface 32 of the oxygen detection element 30 can more intimately come into contact with the air (reference gas).

In the oxygen sensor 10, the outer surface 34 of the oxygen detection element 30 is brought into contact with exhaust gas, or a gas to be measured, and the inner surface 32 of the oxygen detection element 30 is brought into contact with the air, or a reference gas. The oxygen detection element 30 formed of an oxygen-ion-conductive solid electrolyte generates electromotive force by an oxygen concentration cell effect in accordance with differential oxygen concentration between the inner and outer surfaces. The electrical potential of the outer surface 34 of the oxygen detection element 30 is externally output via the external electrode 35 formed on the outer surface 34, the external-electrode terminal member 38, and the sensor output lead wire 39. The electrical potential of the inner surface 32 is externally output via the internal electrode 33 formed on the inner surface 32, the internal-electrode terminal member 37, and the sensor output lead wire 40.

By means of measuring voltage between the sensor output lead wires 39 and 40, the oxygen sensor 10 of Embodiment 1 can detect the oxygen concentration of exhaust gas.

In the oxygen sensor 10 of Embodiment 1, the oxygen detection element 30 is heated by a heater 36 so as to promptly activate its solid electrolyte.

Next, a method of manufacturing the oxygen sensor 10 according to Embodiment 1 will be described. Since a known method may be used except for attachment of the water-repellent filter member 19 and the internal tubular member 20 to the interior of the grommet 17, the attachment of the water-repellent filter member 19 and the internal tubular member 20 to the interior of the grommet 17 will be mainly described, and other work will be briefly described.

First, by use of the insulators 12 and 13 and the ceramic powder 14, the oxygen detection element 30 is crimp-fixed in place in the interior of the metallic shell 11. Next, the protector 43 is laser-attached to the tip end of the metallic shell 11.

Next, the heater 36, the internal-electrode terminal member 37, and the external-electrode terminal member 38 are partially accommodated in the interior of the separator 16, and a tubular, elastic member 22 having a cross-sectional shape resembling the letter J is disposed on an outer surface of the separator 16 located on a side toward the tip end of the oxygen sensor 10 with respect to a flange portion 16b. Then, the lead wires 39, 40, 41, and 42 are inserted through the metallic sleeve 15, and separator 16 is covered by the thus-prepared metallic sleeve 15 from the rear-end side such that an internal projection 15g of the metallic sleeve 15 abuts the flange portion 16b of the separator 16. At this point in time, a separator crimp portion 15f of the metallic sleeve 15 is not yet crimped, but has a diameter so as to allow insertion of the flange portion 16b of the separator 16.

Subsequently, the grommet 17 is fitted to the lead wire 39 and the like and is inserted into a rear end portion of the metallic sleeve 15. At this point in time, a grommet crimp portion 15e of the metallic sleeve 15 is not crimped yet, but has a diameter so as to allow insertion of the grommet 17. The water-repellent filter member 19 and the internal tubular member 20 are disposed in the air through-hole 18 formed at the center of the grommet 17.

The heater 36 to which the internal-electrode terminal member 37 is attached is inserted into the closed-bottomed bore 31 of the oxygen detection element 30, and the tip end portion 15c of the metallic sleeve 15 is caused to abut the hexagonal portion 11r of the metallic shell 11.

A portion of the metallic sleeve 15 that surrounds a portion of the separator 16 extending toward the sensor tip end with respect to the flange portion 16b is crimped, thereby reducing the diameter of the elastic member 22 and forming the separator crimp portion 15f. This causes the elastic member 22 located inside the separator crimp portion 15f to become deformed, thereby elastically holding the flange portion 16b between the elastic member 22 and the internal projection 15g of the metallic sleeve 15 and thus fixing the separator 16 in place within the metallic sleeve 15.

Subsequently, the rear-end grommet crimp portion 15e of the metallic sleeve 15 is crimped and reduced in diameter, thereby fixing the grommet 17 in place in the metallic sleeve 15 in a gastight condition.

In this condition, the tip end portion 15c is externally crimped to temporarily fix the same, and then the tip end portion 15c is laser-welded to the rear-end connection portion 11k of the metallic shell 11.

This completes the oxygen sensor 10 of Embodiment 1.

Next, the filter-attaching process for attaching the water-repellent filter member 19 and the internal tubular member 20 to the interior of the air through-hole 18 of the grommet 17 will be described in detail with reference to FIGS. 2 and 3.

According to the filter-attaching process of Embodiment 1, first, the bottom wall portion 19t and the tubular side wall portion 19s of water-repellent filter member 19 are inserted into the air through-hole 18 of the grommet 17. Next, the tubular portion 20t of the internal tubular member 20 is inserted into the tubular side wall portion 19s of the water-repellent filter member 19 that is already fitted into the air through-hole 18.

By means of, first, inserting the water-repellent filter member 19 and then inserting the internal tubular member 20, as compared with the case where the internal tubular member 20 and the water-repellent filter member 19 covering the internal tubular member 20 are inserted in unison into the air through-hole 18 of the grommet 17, the water-repellent filter member 19 can be inserted into the air through-hole 18 with smaller force. This is because, when the water-repellent filter member 19 is inserted into the air through-hole 18, only the bottom wall portion 19t and the tubular side wall portion 19s thereof are inserted, so that the insertion work is facilitated by virtue of some deformation of the water-repellent filter member 19.

In inserting the internal tubular member 20, the internal tubular member 20 may be inserted in a sliding relation with the tubular side wall portion 19s of the water-repellent filter member 19. As compared with the case of joint insertion of the internal tubular member 20 and water-repellent filter member 19, this renders the pressing force required for insertion smaller. Furthermore, in the course of inserting the internal tubular member 20, little stress is imposed on the bottom wall portion 19t of the water-repellent filter member 19 and the shoulder portion 19k located between the bottom wall portion 19t and the tubular side wall portion 19s of water-repellent filter member 19. Therefore, the occurrence of deformation or breakage, such as cracking, can be reliably prevented with respect to the bottom wall portion 19t and the shoulder portion 19k of the water-repellent filter member 19, which are conventionally apt to suffer cracking or the like.

As described below, the water-repellent filter member 19 used in the oxygen sensor 10 of Embodiment 1 is formed by subjecting a resin sheet of a porous, fibrous structure having air permeability and water repellency to forming work, and has tubular side wall portion 19s and a bottom wall portion 19t. As compared with a resin sheet, the water-repellent filter member 19 can be handled more easily.

The water-repellent filter member 19 has a formed tubular side wall portion 19s and is free of wrinkled resin sheet portions found in conventional structures. Accordingly, in the filter-attaching process, even when the water-repellent filter member 19 and the internal tubular member 20 covered with the same are inserted in unison into the air through-hole 18 of the grommet 17, the insertion work can be performed under a smaller load as compared with the conventional practice in which an unformed resin sheet is pressed in by use of an internal tubular member. Accordingly, the load imposed on the shoulder portion 19k can be reduced, thereby preventing the occurrence of cracking (breakage) in the shoulder portion 19k.

Next, a method of manufacturing the above-described water-repellent filter member will be described with reference to FIGS. 7(a) and 7(b).

The method of manufacturing a water-repellent filter member of Embodiment 1 employs a manufacturing apparatus 50 for manufacturing a water-repellent filter member from the resin sheet 54 by thermoforming. The manufacturing apparatus 50 includes a female die member 51 and a male die member 52. The female die member 51 has a forming hole 51k having the form of a round through-hole and adapted for thermoforming the resin sheet 54. The male die member 52 has a hollow, cylindrical rodlike portion 52b disposed on the axis of the forming hole 51k of the female die member 51. In order to insert the rodlike portion 52b into the forming hole 51k and to draw out the rodlike portion 52b from the forming hole 51k, the male die member 52 is vertically movable relative to the female die member 51 on the axis of the forming hole 51k. The forming hole 51k of the female die member 51 has a diameter slightly greater than the outside diameter of the rodlike portion 52b. Heaters 51h are embedded in a portion of the female die member 51 located radially outward of the wall surface of the forming hole 51k and are adapted to heat the wall surface of the forming hole 51k so as to heat the resin sheet 54.

The resin sheet 54 has a porous, fibrous structure having air permeability and water repellency. Specifically, the present embodiment employs a resin sheet formed of a fluorine-containing resin such as PTFE and to which both water repellency and air permeability are imparted by forming fine clearances (pores) among water-repellent fibers. More specifically, the resin sheet of the present embodiment is made of, for example, GORE-TEX or POREFLON.

Figure 7A:
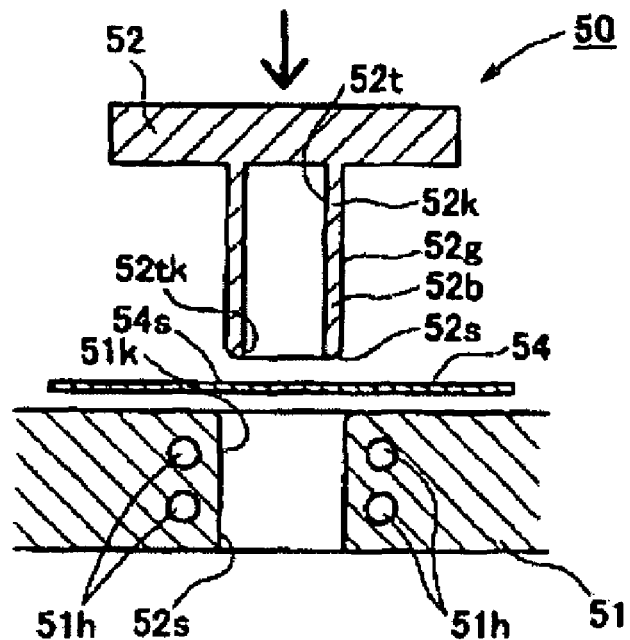

The resin sheet 54 is placed between the female die member 51 and the male die member 52 (rodlike portion 52b) of the manufacturing apparatus 50 for manufacturing the water-repellent filter member 19 (see FIG. 7(a)). While a tip end 52s of the rodlike portion 52b of the male die member 52 is pressed against a sheet projectional-end portion 54s of the resin sheet 54, the resin sheet 54, together with the rodlike portion 52b, is inserted under pressure into the forming hole 51k. This causes the resin sheet 54 to cover the rodlike portion 52b of the male die member 52 so as to cover the tip end 52s of the rodlike portion 52b and a radially outer circumferential surface 52g of the rodlike portion 52b.

Figure 7B:
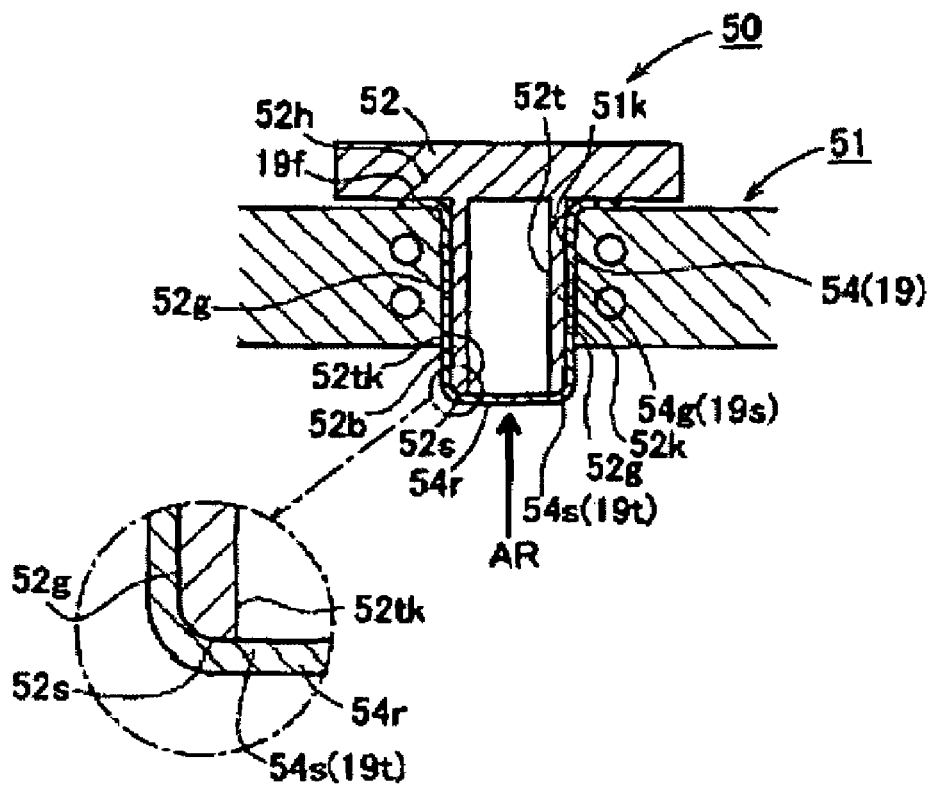

As shown in FIG. 7(b), the rodlike portion 52b is inserted such that the tip end 52s and vicinity thereof and the sheet projectional-end portion 54s of the resin sheet 54 located axially ahead (downward in FIG. 7(b)) of the tip end 52s project from the forming hole 51k of the female die member 51.

In this manner, the water-repellent filter member 19 is formed.

Specifically, a base-end-side portion 52k of the rodlike portion 52b is defined as a portion of the rodlike portion 52b that is biased from the tip end 52s toward the base end of the rodlike portion 52b (upward direction in FIGS. 7(a) and 7(b)) and is located within the forming hole 51k. A base-end-side circumferential portion 54g of the resin sheet 54 is defined as a portion of the resin sheet 54 located radially outward (leftward and rightward in FIGS. 7(a) and 7(b)) of the base-end-side portion 52k. The base-end-side circumferential portion 54g is heated and then solidified whereby the tubular side wall portion 19s can be formed.

The profile of a portion of the tubular side wall portion 19s of the formed water-repellent filter member 19 that corresponds to the base-end-side circumferential portion 54g is not influenced by wrinkled portions of the resin sheet appearing during the course of forming, and undergoes forming while being profiled to assume a shape imparted by the pressing die (female die member 51). Therefore, the water-repellent filter member 19 having a desired profile can be formed.

Figure 6A:
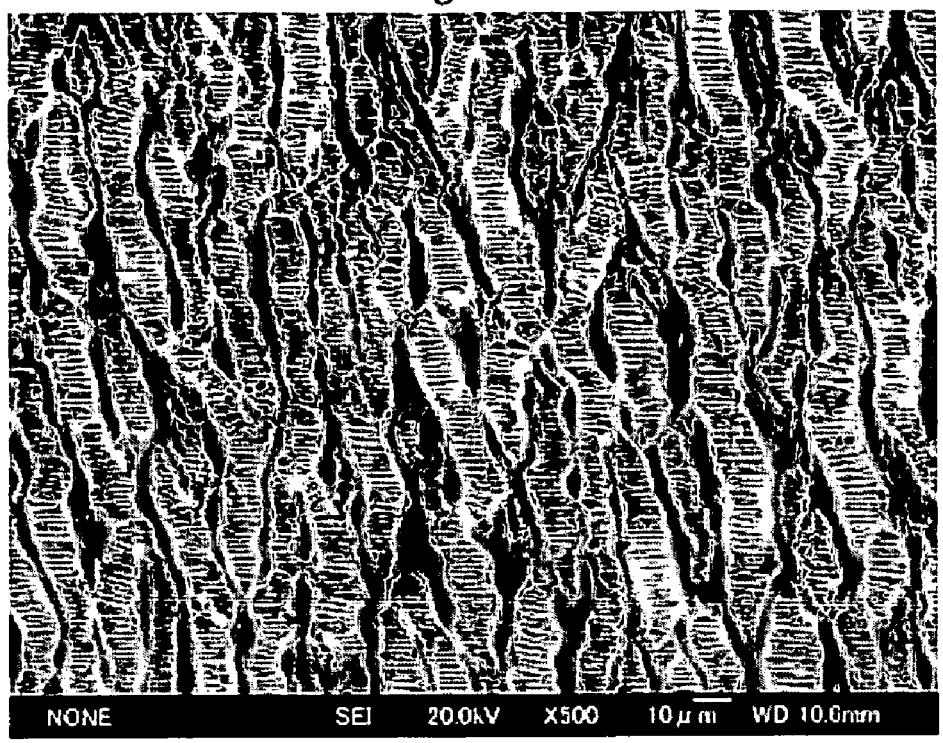
Figure 6B:
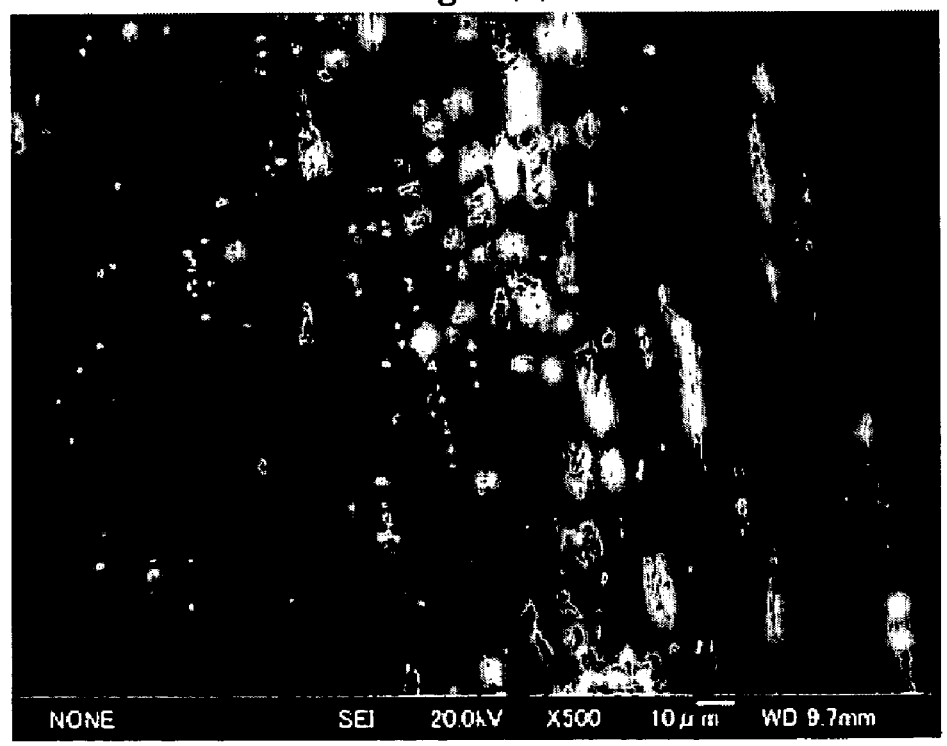

As shown in FIG. 6(b), at the tubular side wall portion 19s, fibers of the resin sheet 54 are fused together, so that fibers and clearances (pores) are almost no longer present. In other words, the tubular side wall portion 19s is substantially a resin plate of PTFE. Accordingly, the tubular side wall portion 19s has no air permeability, but has rigidity. By virtue of the rigidity of the tubular side wall portion 19s, the water-repellent filter member 19 can maintain a shape resembling a top hat. As described previously, this allows the water-repellent filter member 19 alone to be singly inserted into the air through-hole 18 of the grommet 17.

A portion of the resin sheet 54 held between the female die member 51 and a body portion 52h of the male die member 52 also undergoes thermoforming and becomes the flange portion 19f.

A portion of the resin sheet 54 that will become the bottom wall portion 19t of the water-repellent filter member 19; i.e., the sheet projectional-end portion 54s located axially outside of the tip end 52s of the rodlike portion 52b of the male die member 52, assumes the following form. A noncontact portion 54r of the sheet projectional-end portion 54s is a portion of the sheet projectional-end portion 54s that corresponds to an opening 52tk of a hollow portion 52t of the rodlike portion 52b; in other words, a portion of the sheet projectional-end portion 54s that is surrounded by a portion of the sheet projectional-end portion 54s in contact with the tip end 52s of the rodlike portion 52b. The noncontact portion 54r not in contact with the rodlike portion 52b is held at relatively low temperature so as not to cause mutual fusion of fibers of the porous, fibrous structure. This is because heat is unlikely to be transmitted to the noncontact portion 54r from the rodlike portion 52b.

Thus, at least the noncontact portion 54r maintains the porous, fibrous structure of the resin sheet 54 and thus can have air permeability as well as water repellency. The water-repellent filter member 19 whose bottom wall portion 19t is formed of the sheet projectional-end portion 54s including the noncontact portion 54r maintains, at its bottom wall portion 19t, the porous, fibrous structure as shown in FIG. 6(a) and thus can have appropriate air permeability.

The manufacturing method of the present embodiment can form the tubular side wall portion 19s by use of the resin sheet 54 and can reliably manufacture the water-repellent filter member 19 in which, even after forming work, at least a portion of the bottom wall portion 19t maintains the porous, fibrous structure of the resin sheet 54.

Since the noncontact portion 54r does not contact the rodlike portion 52b, in the course of forming the water-repellent filter member 19, no pressure in the thickness direction (vertical direction in FIGS. 7(a) and 7(b)) is imposed on the noncontact portion 54r. Accordingly, the noncontact portion 54r is also free from deformation of the porous, fibrous structure, which could otherwise result from application of pressure.

Thus, the method of manufacturing a water-repellent filter member of Embodiment 1 can reliably provide a water-repellent filter member 19 that has air permeability at the bottom wall portion 19t.

More preferably, as indicated by the arrow in FIG. 7(b), air AR having a temperature, such as room temperature, sufficiently lower than the melting temperature of the resin sheet 54 is blown against the sheet projectional-end portion 54s (noncontact portion 54r) of the resin sheet 54. The air AR further suppresses temperature rise of the sheet projectional-end portion 54s, thereby reliably preventing fusion of fibers at the sheet projectional-end portion 54s. In place of the air AR, water or the like may be sprayed on or brought into contact with the sheet projectional-end portion 54s.

In Embodiment 1 described above, the water-repellent filter member 19 is formed using the female die member 51 and the male die member 52 shown in FIGS. 7(a) and 7(b). However, other methods (Modified Embodiments 1 and 2) may be used to form the water-repellent filter member 19. These manufacturing methods will be described below.

Modified Embodiment 1

A method of manufacturing the water-repellent filter member 19 according to Modified Embodiment 1 will be described with reference to FIGS. 8(a)-8(c). In Embodiment 1 described previously, the cylindrical rodlike portion 52b and the resin sheet 54 are inserted together under pressure into the forming hole 51k. Modified Embodiment 1 differs from Embodiment 1 as follows. A female die member 61 is split into a first and second female die members 61x and 61y such that a forming hole 61k is halved. The first and second female die members 61x and 61y can be moved away from each other (in a lateral direction, as shown). After a rodlike portion 62b of a male die member 62 is covered with the resin sheet 64, the first and second female die members 61x and 61y which have been moved away from each other in advance are joined together from a position radially outside the rodlike portion 62b, to thereby form the forming hole 61k. In this manner, the first and second female die members 61x and 61y thermoform a portion of the resin sheet 64 located radially outward of the rodlike portion 62b by application of heat and pressure.

Accordingly, different features are mainly described, and description of like features is omitted or briefly described.

The method of manufacturing the water-repellent filter member 19 according to Modified Embodiment 1 uses a manufacturing apparatus 60 for manufacturing the water-repellent filter member 19 from the resin sheet 64 by thermoforming as in the case of Embodiment 1. The manufacturing apparatus 60 includes the male die member 62 having a hollow, cylindrical rodlike portion 62b similar to that of Embodiment 1 and the female die member 61 having the forming hole 61k. The female die member 61 as a whole has the forming hole 61k and is halved into the first and second female die members 61x and 61y by a plane passing along the axis of the forming hole 61k. Accordingly, the first and second female die members 61x and 61y have first and second semicylindrical recesses 61u and 61v, respectively. The first and second female die members 61x and 61y are movable in opposite directions on a line perpendicular to the axis of the forming hole 61k. When the first and second female die members 61x and 61y are joined together (see FIG. 8(c)), the first and second semicylindrical recesses 61u and 61v are also joined together to form a single forming hole 61k. The forming hole 61k has a diameter slightly greater than the outside diameter of the rodlike portion 62b. Heaters 61h are embedded in portions of the first and second female die members 61x and 61y located radially outward of the surfaces of the first and second semicylindrical recesses 61u and 61v, and are adapted to heat the surfaces of the first and second semicylindrical recesses 61u and 61v so as to heat the resin sheet 64.

Figure 8A:
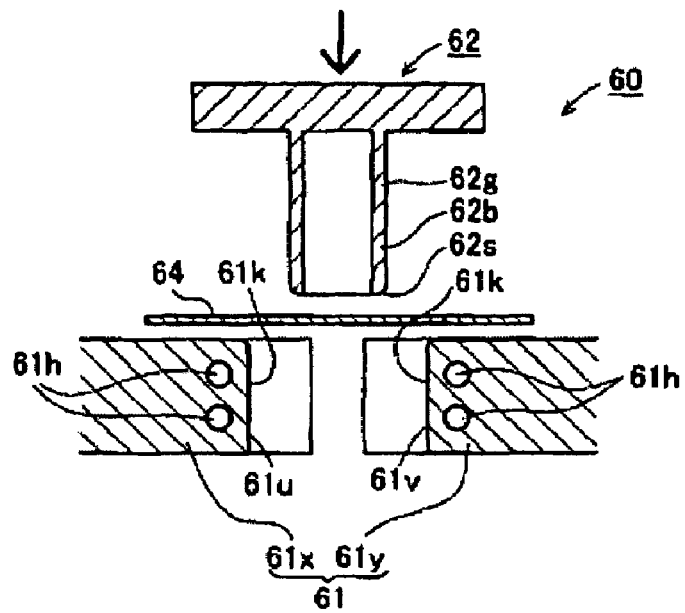

According to the manufacturing method of Modified Embodiment 1, first, the first and second female die members 61x and 61y of the female die member 61 are moved away from one another in the left-right (lateral) directions in FIG. 8(a). In this condition, the resin sheet 64 is placed between the female die member 61 and the male die member 62 (rodlike portion 62b). Subsequently, the male die member 62 is lowered such that a tip end 62s of the rodlike portion 62b thereof is pressed against a sheet projectional-end portion 64s of the resin sheet 64. This causes the resin sheet 64 to cover the rodlike portion 62b of the male die member 62 in such manner as to cover the tip end 62s of the rodlike portion 62b and a radially outer circumferential surface 62g of the rodlike portion 62b (see FIG. 8(b)). In Modified Embodiment 1, the resin sheet 64 reaches a body portion 62h of the male die member 62.

Figure 8B:
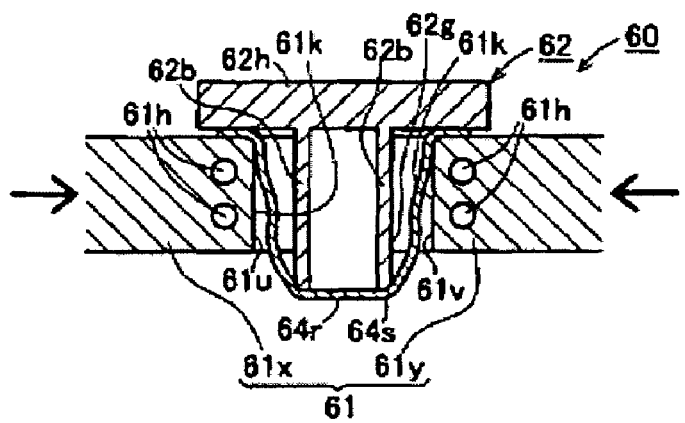
Figure 8C:
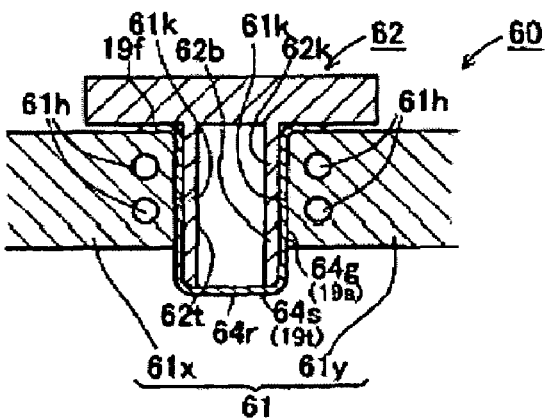

As in the case of Embodiment 1, as shown in FIG. 8(b), the rodlike portion 62b is lowered until the tip end 62s and vicinity thereof and the sheet projectional-end portion 64s of the resin sheet 64 located axially ahead (downward in FIG. 8(b)) of the tip end 62s project downward from the female die member 61 (first and second female die members 61x and 61y).

Next, the first and second female die members 61x and 61y of the female die member 61 are caused to approach the rodlike portion 62b from a radially outside direction and are joined together. A base-end-side portion 62k of the rodlike portion 62b of the male die member 62 is defined as a portion of the rodlike portion 62b that is biased from the tip end 62s toward the base end of the rodlike portion 62b (upward in FIG. 8(c)) and is located within the forming hole 61k of the female die member 61. A base-end-side circumferential portion 64g of the resin sheet 64 is defined as a portion of the resin sheet 64 located radially outward (leftward and rightward in FIG. 8(c)) of the base-end-side portion 62k. With the first and second female die members 61*x* and 61*y* joined together, the base-end-side circumferential portion 64*g* of the resin sheet 64 is pressed from a radially outside direction and is heated and solidified, whereby the tubular side wall portion 19*s* can be formed.

As in the case of Embodiment 1, a portion of the resin sheet 64 held between the female die member 61 and the body portion 62*h* of the male die member 62 also undergoes thermoforming and to become the flange portion 19*f*.

A portion of the resin sheet 64 that will become the bottom wall portion 19*t* of the water-repellent filter member 19; i.e., the sheet projectional-end portion 64*s* located axially outside of the tip end 62*s* of the rodlike portion 62*b* of the male die member 62, assumes a form similar to that of Embodiment 1. A portion of the sheet projectional-end portion 64*s* that does not contact the rodlike portion 62*b* because of presence of a hollow portion 62*t*; i.e., a noncontact portion 64*r*, is held at a relatively low temperature so as not to cause mutual fusion of fibers of the porous, fibrous structure. Thus, the noncontact portion 64*r* maintains the porous, fibrous structure, so that, as in the case of Embodiment 1, the bottom wall portion 19*t* of the water-repellent filter member 19 can retain air permeability.

Accordingly, the manufacturing method of Modified Embodiment 1 can also reliably manufacture the water-repellent filter member 19.

In Embodiment 1 described above, the rodlike portion 52*b* and the resin sheet 54 are inserted together under pressure into the forming hole 51*k*. Thus, in the course of inserting under pressure, stress is apt to be imposed on the resin sheet 54, particularly on a portion (which will become the shoulder portion 19*k*; see FIG. 3) located in the vicinity of the tip end 52*s* of the tubular portion 52*b*. This involves a risk of cracking, deformation, or the like at that portion.

By contrast, the method of manufacturing the water-repellent filter member 19 of Modified Embodiment 1 uses split type first and second female die members 61*x* and 61*y*. The resin sheet 64 is caused to cover the tip end 62*s* of the rodlike portion 62*b*. Subsequently, by moving the first and second female die members 61*x* and 61*y*, the base-end-side circumferential portion 64*g* of the resin sheet 64 located radially outward of the rodlike portion 62*b* is pressed against the rodlike portion 62*b* from a radially outside direction and is heated. Accordingly, stress is not imposed on a portion of the water-repellent filter member 19 that will become the shoulder portion 19*k*, so that cracking or the like hardly occurs.

Modified Embodiment 2

A method of manufacturing a water-repellent filter member according to Modified Embodiment 2 will next be described with reference to FIGS. 9(*a*) and 9(*b*). In Embodiment 1 described previously, the cylindrical rodlike portion 52*b* is used; the resin sheet 54 has a noncontact portion 52*r*, which does not contact the rodlike portion 52*b*; and through separation of the noncontact portion 52*r* from the rodlike portion 52*b*, transmission of heat from the rodlike portion 52*b* to the noncontact portion 52*r* is prevented. Modified Embodiment 2 differs from Embodiment 1 as follows. Modified Embodiment 2 employs a solid rodlike portion 72*b*. A sheet projectional-end portion 74*s* of a resin sheet 74 is held between a tip end 72*s* of the rodlike portion 72*b* and an abutment face 73*s* of a heat release member 73. Release of heat from the heat release member 73 prevents a temperature rise of the sheet projectional-end portion 74*s*, thereby preventing fusion of fibers.

Accordingly, different features are mainly described, and description of like features is omitted or briefly described.

The method of manufacturing the water-repellent filter member 19 according to Modified Embodiment 2 employs a manufacturing apparatus 70 for manufacturing the water-repellent filter member 19 from the resin sheet 74 by thermoforming as in the case of Embodiment 1. The manufacturing apparatus 70 includes a female die member 71 and a male die member 72. The female die member 71 has a forming hole 71*k* having the form of a round through-hole. The male die member 72 has a substantially cylindrical, solid rodlike portion 72*b* disposed on the axis of the forming hole 71*k* and having a diameter slightly smaller than that of the forming hole 71*k*. The manufacturing apparatus 70 further includes a substantially columnar heat release member 73 disposed on the axis of the forming hole 71*k*, located axially ahead (downward in FIGS. 9(*a*) and 9(*b*)) of the tip end 72*s* of the rodlike portion 72*b*, and having a diameter slightly smaller than that of the forming hole 71*k*. The male die member 72 and the heat release member 73 are movable on the axis (in the vertical direction in FIGS. 9(*a*) and 9(*b*)) of the forming hole 71*k*. As in the case of Embodiment 1, heaters 71*h* are embedded in a portion of the female die member 71 located radially outward of the wall surface of the forming hole 71*k* and are adapted to heat the resin sheet 74.

Figure 9A:
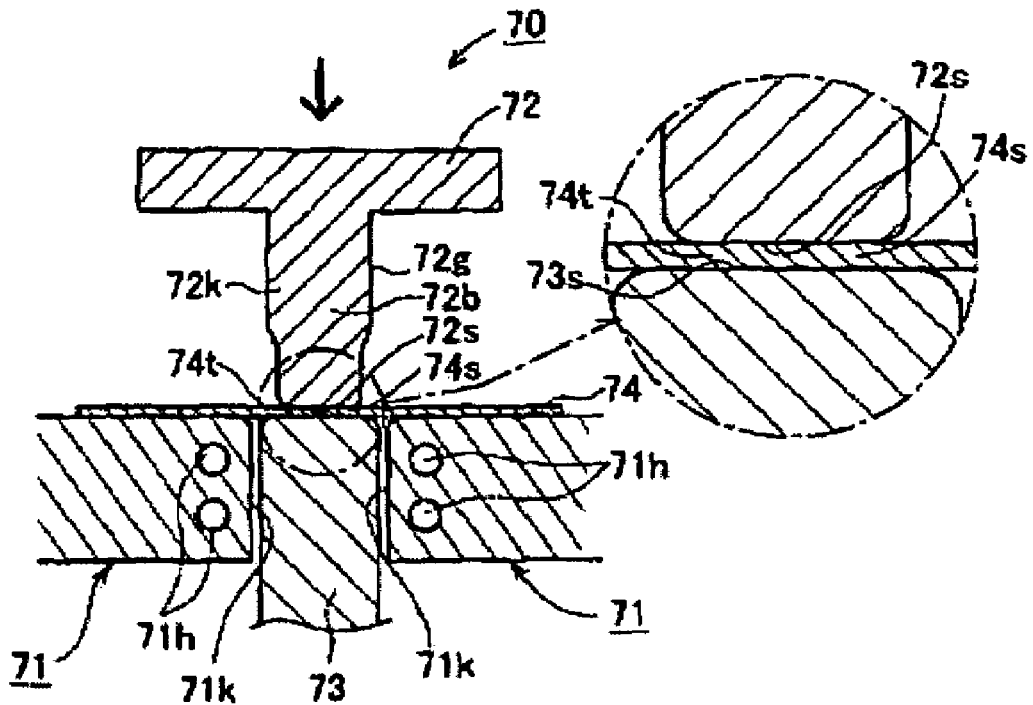
Figure 9B:
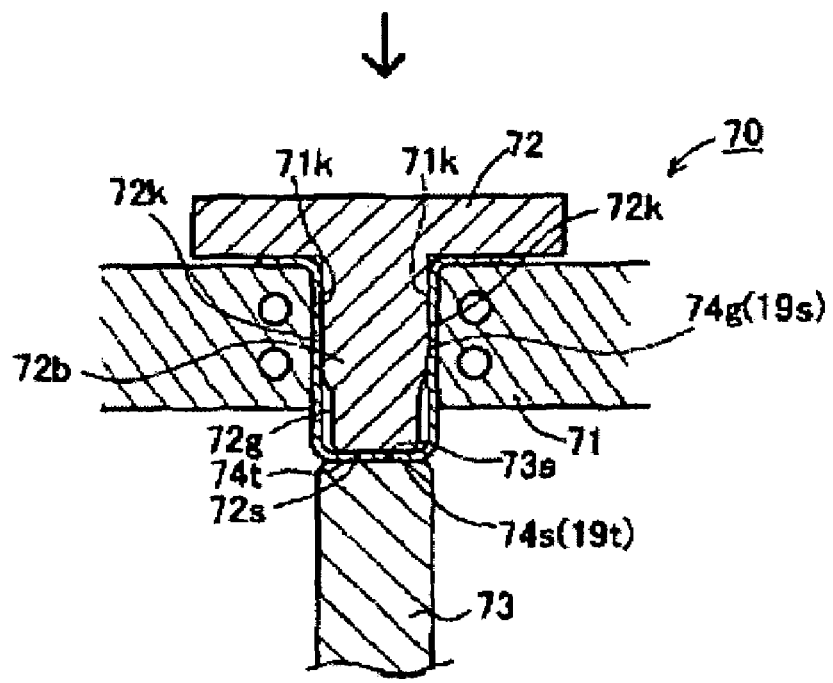

As shown in FIG. 9(*a*), according to the manufacturing method of Modified Embodiment 2, the resin sheet 74 is placed between the female die member 71 and the rodlike portion 72*b* of the male die member 72. Subsequently, the tip end 72*s* of the rodlike portion 72*b* is pressed against the sheet projectional-end portion 74*s* of the resin sheet 74, and the base-end (the top in FIG. 9(*a*)) abutment face 73*s* of the heat release member 73 is also pressed against at least a portion, or an abutment portion 74*t*, of the sheet projectional-end portion 74*s*, thereby holding the sheet projectional-end portion 74*s* (abutment portion 74*t*) between the tip end 72*s* of the rodlike portion 72*b* and the abutment face 73*s* of the heat release member 73.

The heat release member 73 is formed of a material having good heat conductivity, such as copper, and provides such heat release performance so as to maintain a temperature sufficiently lower than the melting temperature of the resin sheet 74.

While the abutment portion 74*t* of the resin sheet 74 is held between the tip end 72*s* of the rodlike portion 72*b* and the abutment face 73*s* of the heat release member 73, the rodlike portion 72*b* (male die member 72) and the heat release member 73 are synchronously moved in such manner so as to move the abutment portion 74*t* of the resin sheet 74 toward the tip-end side (downward in FIGS. 9(*a*) and 9(*b*)) along the axial direction of the forming hole 71*k*. This causes the resin sheet 74 to be inserted under pressure into the forming hole 71*k*.

As in the case of Embodiment 1, as shown in FIG. 9(*b*), the rodlike portion 72*b* is lowered until the tip end 72*s* and vicinity thereof and the sheet projectional-end portion 74*s* of the resin sheet 74 located axially ahead (downward in FIG. 8(*b*)) of the tip end 72*s* project downward from the female die member 71.

In this manner, the water-repellent filter member 19 is formed. Specifically, as in the case of Embodiment 1, a base-end-side portion 72*k* of the rodlike portion 72*b* is defined as a portion of the rodlike portion 72*b* that is biased from the tip end 72*s* toward the base end of the rodlike portion 72*b* (upward in FIGS. 9(*a*) and 9(*b*)) and is located within the forming hole 71*k*. A base-end-side circumferential portion 74*g* of the resin sheet 74 is defined as a portion of the resin sheet 74 located radially outward of a circumferential surface 72g of the base-end-side portion 72k. The base-end-side circumferential portion 74g is heated and then solidified, whereby the tubular side wall portion 19s can be formed.

At least a portion of the sheet projectional-end portion 74s (which will become the bottom wall portion 19t of the water-repellent filter member 19) of the resin sheet 74 abuts the abutment face 73s of the heat release member 73. Accordingly, even when the rodlike portion 72b and its tip end 72s rise in temperature, at least the portion of the sheet projectional-end portion 74s is held at a relatively low temperature so as not to cause mutual fusion of fibers of the porous, fibrous structure.

Thus, the abutment portion 74t can be free from mutual fusion of the fibers. The bottom wall portion 19t of the formed water-repellent filter member 19 retains a porous, fibrous structure of the resin sheet and thus can have air permeability. In this manner, the method of manufacturing a water-repellent filter member of the present invention can reliably provide the water-repellent filter member 19 that has air permeability at the bottom wall portion 19t.

In Modified Embodiment 2, in order to reduce stress imposed on an edge portion of the sheet projectional-end portion 74s (which abuts the tip end 72s) of the resin sheet 74, the rodlike portion 72b of the male die member 72 is configured such that the tip end 72s and vicinity thereof are slightly smaller in diameter than the base-end-side portion 72k. This prevents the following problem: at the initial stage of inserting the rodlike portion 72b into the forming hole 71k, insertion resistance arises on the resin sheet 74 held between the rodlike portion 72b and the forming hole 71k and imposes a high stress on the edge portion of the sheet projectional-end portion 74s.

Embodiment 2

Next, an oxygen sensor 110 according to Embodiment 2 will be described with reference to FIGS. 1 and 10 to 13. The oxygen sensor 110 according to Embodiment 2 differs from the oxygen sensor 10 of Embodiment 1 only in that the oxygen sensor 110 employs a water-repellent filter member 200 that is a single member obtained by integrally forming the two members, or the water-repellent filter member 19 and the internal tubular member 20, of the oxygen sensor 10 of Embodiment 1. Thus, those features different from those of Embodiment 1 are mainly described, and description of like features is omitted or briefly described.

Figure 10:
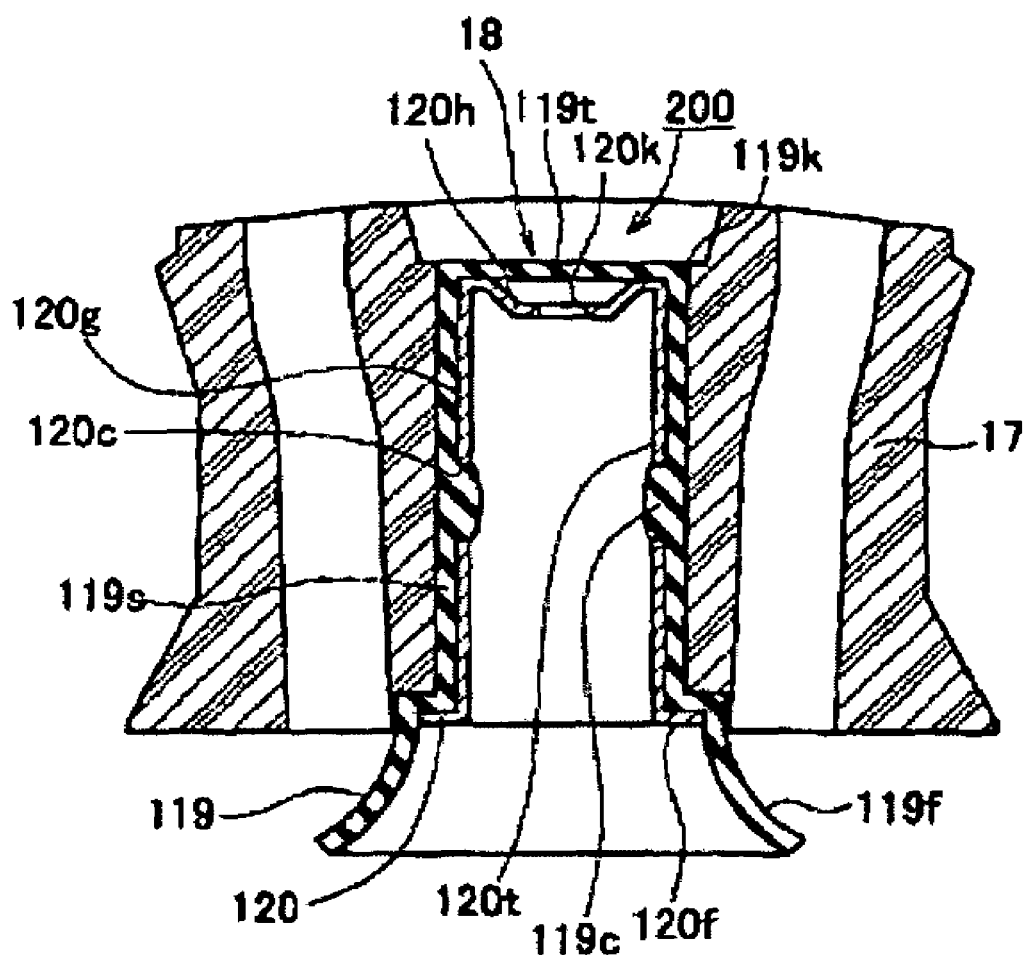
FIG. 10 is a vertical sectional view showing an assembled condition of a grommet, an internal tubular member, and a water-repellent filter member according to Embodiment 2.

As shown in FIG. 10, the water-repellent filter member 200 used in the oxygen sensor 110 is attached to the interior of the air through-hole 18 of the grommet 17. In contrast to Embodiment 1, the water-repellent filter member 200 assumes an integral form of the resin member 119 and the internal tubular member 120 (FIG. 12).

Figure 11:
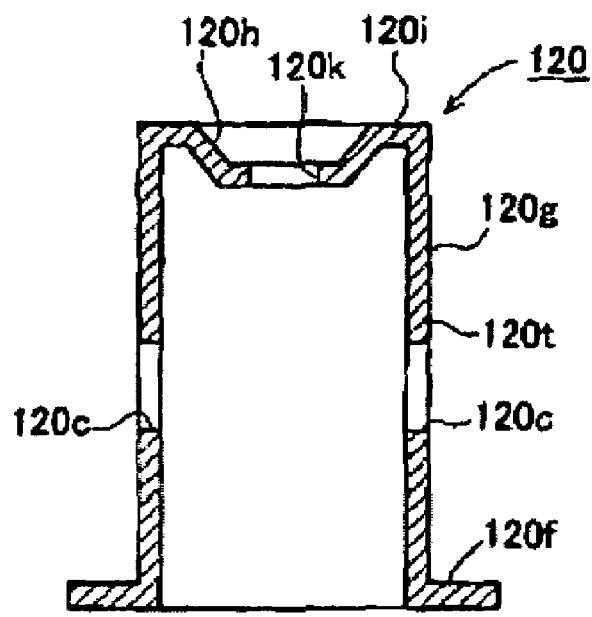
FIG. 11 is a vertical sectional view of the internal tubular member according to Embodiment 2.

As in the case of the internal tubular member 20 of Embodiment 1, the internal tubular member 120 is formed of stainless steel and, as shown in FIG. 11, assumes a shape resembling a top hat. The internal tubular member 120 has a tubular portion 120t. The tubular portion 120t has an internal flange portion 120h extending radially inward at a first axial end (the top in FIG. 11) 120i. The internal flange portion 120h has a first-end-side opening portion 120k at its center. Accordingly, the internal tubular member 120 has a tubular form and allows air communication therethrough past the first end thereof and the second end thereof. Also, in the internal tubular member 120 of Embodiment 2, the internal flange portion 120h is depressed toward the second axial end (the bottom in FIG. 11) with respect to the first end 120i, so that the first-end-side opening portion 120k is biased from the first end 120i toward the second axial end (the bottom in FIG. 11). Also, the internal tubular member 120 has a flange portion 120f projecting radially outward from the second end (lower end in FIG. 11) of the tubular portion 120t. Furthermore, in contrast to Embodiment 1, the internal tubular member 120 of Embodiment 2 has a plurality of through-holes 120c extending through an axially central portion of the tubular portion 120t in its thickness direction and arranged in a circumferentially spaced condition.

Figure 12:
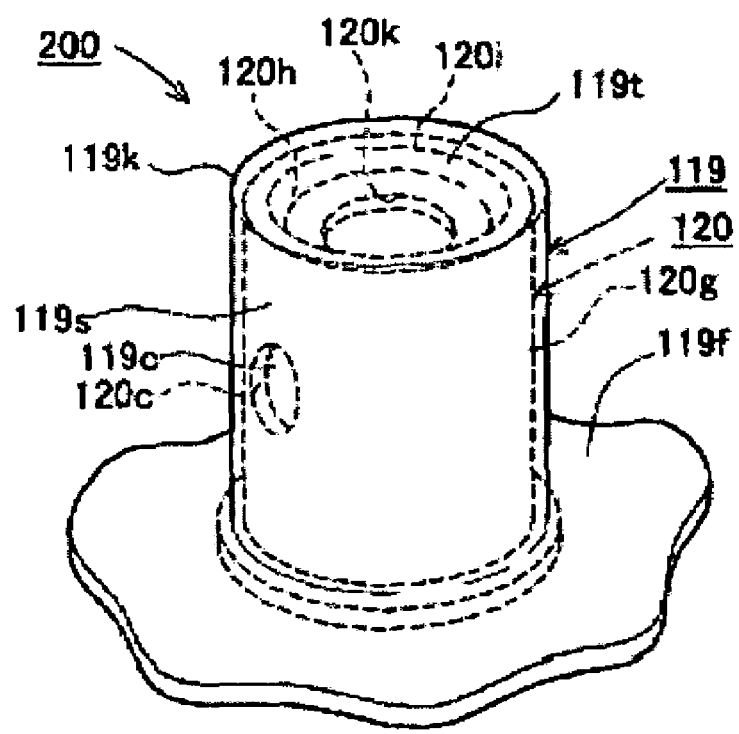
FIG. 12 is a perspective, phantom view of the water-repellent filter member according to Embodiment 2.

As is understood from FIGS. 10 and 12, the resin member 119 is formed so as to cover the outer surface of the internal tubular member 120 described above and assumes a shape resembling a top hat (closed-bottomed cylindrical shape). The resin member 119 is formed of a resin sheet 84 of GORE-TEX (trade name) of the porous, fibrous structure having air permeability and water repellency by a forming process described below. The resin member 119 encloses the internal tubular member 120 and is integrally formed with the internal tubular member 120. The resin member 119 includes an axially (vertically, in the drawing) extending tubular side wall portion 119s having a cylindrical shape and a disklike bottom wall portion 119t that closes one end of the tubular side wall portion 119s. The resin member 119 further includes a flange portion 119f extending radially outward from an end of the tubular side wall portion 119s opposite the bottom wall portion 119t. Since the bottom wall portion 119t is formed in such manner as to hold the porous, fibrous structure of the resin sheet 84 (see FIG. 6(a)), the resin member 119 functions as a portion of the water-repellent filter member 200 that has air permeability at the bottom wall portion 119t.

Furthermore, in the water-repellent filter member 200 of Embodiment 2, portions of the tubular side wall portion 119s of the resin member 119 that overlie the through-holes 120c of the internal tubular member 120 enclosed by the resin member 119 partially protrude into the through-holes 120c, thereby forming engagement portions 119c that project radially inward. Thus, the resin member 119 and the internal tubular member 120 are integrated with one another and do not separate from each other.

Next, a method of manufacturing the oxygen sensor 110 according to Embodiment 2 will be described. The method of manufacturing the oxygen sensor 110 according to Embodiment 2 differs from the method of manufacturing the oxygen sensor 10 of Embodiment 1 only in that the water-repellent filter member 200 is employed in place of the water-repellent filter member 19 and the internal tubular member 20. Thus, only a filter-attaching process for attaching the water-repellent filter member 200 to the interior of the air through-hole 18 of the grommet 17 is described, and description of other features is omitted.

According to Embodiment 2, in the filter-attaching process, the water-repellent filter member 200 is inserted into the grommet 17.

In the water-repellent filter member 200, the engagement portions 119c of the resin member 119 and the through-holes 120c of the internal tubular member 120 are engaged with one another, so that the resin member 119 is unlikely to be detached from the internal tubular member 120. In contrast to Embodiment 1 that requires handling of two members; i.e., the water-repellent filter member 19 and the internal tubular member 20, Embodiment 2 allows attachment of the single water-repellent filter member 200 to the grommet 17, thereby facilitating handling work.

When the water-repellent filter member 200 is inserted into the air through-hole 18 of the grommet 17, insertion resistance imposed on the resin member 119 can be reliably dispersed to the internal tubular member 120 in contrast to the case of using the water-repellent filter member 19 (which has no engagement portions 119c) and the internal tubular member 20 (which has no through-holes 120c) of Embodiment 1. Accordingly, stress imposed on the bottom wall portion 119t and a shoulder portion 119k of the resin member 119 can be further reduced, so that occurrence of cracking or the like in these portions can be more reliably prevented.

Furthermore, the water-repellent filter member 200 has a flange portion 120f provided on the internal tubular member 120. When water-repellent filter member 200 is inserted into the air through-hole 18 of the grommet 17, the flange portion 120f can fix the insertion depth. Therefore, the water-repellent filter member 200 can be readily attached to the air through-hole 18.

Next, a method of manufacturing the water-repellent filter member 200 for use in the oxygen sensor 110 of Embodiment 2 will be described. The method of manufacturing the water-repellent filter member 200 uses a manufacturing apparatus 80 shown in FIGS. 13(a) to 13(c) for manufacturing the water-repellent filter member 200. By use of the manufacturing apparatus 80, the internal tubular member 120 is covered with the resin sheet 84, and the resultant assembly is subjected to integral forming; i.e., pressing from a radially outside direction and heating.

The manufacturing apparatus 80 for manufacturing water-repellent filter member 200 includes a female die member 81 and a tube rest 82. The female die member 81 has a forming hole 81k into which the resin sheet 84 and the internal tubular member 120 are inserted for undergoing integral forming. The tube rest 82 is disposed on the axis of the forming hole 81k and below the female die member 81 and has a projectional fixing portion 82b. The tube rest 82 is vertically (in the vertical direction in FIGS. 13(a) to 13(c)) movable on the axis of the forming hole 81k. As in the case of Modified Embodiment 1 described previously, the female die member 81 is halved into first and second female die members 81x and 81y by a plane passing along the axis of the forming hole 81k. The first and second female die members 81x and 81y have first and second semicylindrical recesses 81u and 81v, respectively. The first and second female die members 81x and 81y are movable in opposite directions on a line perpendicular to the axis of the forming hole 81k. When the first and second female die members 81x and 81y are joined together (see FIG. 13(c)), the first and second semicylindrical recesses 81u and 81v are also joined together and form a single forming hole 81k. The forming hole 81k has a diameter slightly greater than the outside diameter of the internal tubular member 120. Heaters 81h are embedded in portions of the first and second female die members 81x and 81y located radially outward of the surfaces of the first and second semicylindrical recesses 81u and 81v and are adapted to heat the surfaces of the first and second semicylindrical recesses 81u and 81v so as to heat the resin sheet 84.

According to the method of manufacturing the water-repellent filter member 200 of Embodiment 2, first, the internal tubular member 120 is fitted onto the projectional fixing portion 82b of the tube rest 82 such that the flange portion 120f of the internal tubular member 120 comes into contact with the tube rest 82. Then, the resin sheet 84 is placed on the internal tubular member 120 and is caused to cover the internal tubular member 120 in such manner as to cover a first-end-side opening portion 120k of a first end 120i of the internal tubular member 120, a portion of an outer circumferential surface 120g of the internal tubular member 120 located on the side toward the first end 120i, and the through-holes 120c (see FIG. 13(b)). In Embodiment 2, the resin sheet 84 reaches a body portion 82h of the tube rest 82.

Figure 13A:
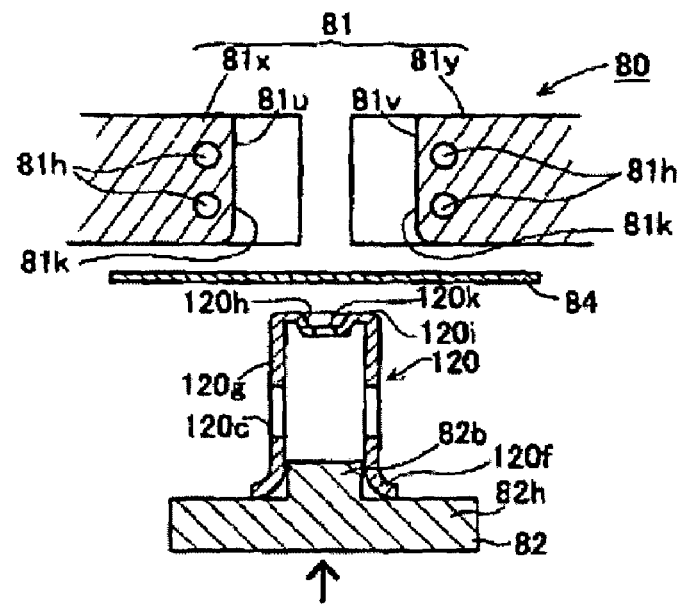
Figure 13B:
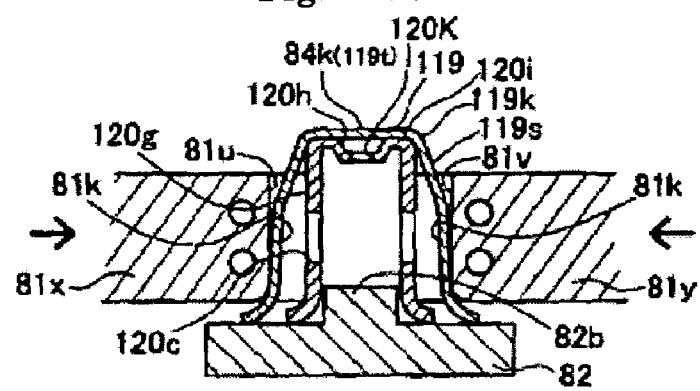
Figure 13C:
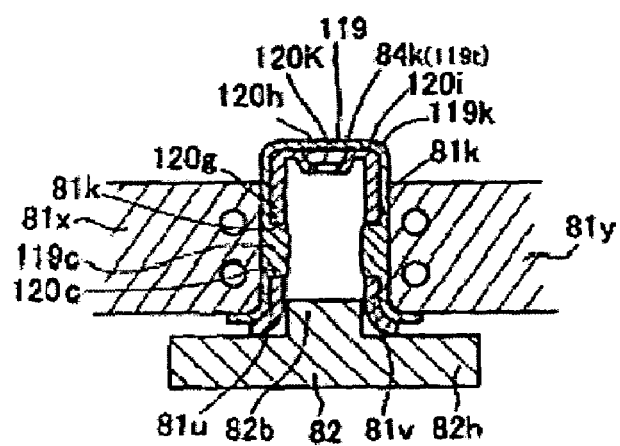

As in the case of Embodiment 1, as shown in FIG. 13(b), the tube rest 82 and the internal tubular member 120 are raised until the first end 120i of the internal tubular member 120 and vicinity thereof and an aperture-closing portion 84k of the resin sheet 84 located axially outward (upward in FIGS. 13(a) to 13(c)) of the first end 120i and closing the first-end-side opening portion 120k project upward from the female die member 81 (first and second female die members 81x and 81y).

Next, the first and second female die members 81x and 81y of the female die member 81 are caused to approach the internal tubular member 120 from a radially outside direction (from right and left in FIGS. 13(a) to 13(c)) and are joined together. A portion of the internal tubular member 120 and a portion of the resin sheet 84 covering the outer circumferential surface of the internal tubular member 120 that are located within the forming hole 81k of the female die member 81 are pressed and heated; i.e., undergo thermoforming. At this time, portions of the resin sheet 84 are fluidized and enter the through-holes 120c of the internal tubular member 120, thereby forming the engagement portions 119c of the resin member 119.

As in the case of Embodiment 1, a portion of the resin sheet 84 held between the female die member 81 and the body portion 82h of the tube rest 82 also undergoes thermoforming to become the flange portion 119f.

Since the internal flange portion 120h of the internal tubular member 120 is depressed, the aperture-closing portion 84k (which closes the one-end side opening portion 120K of the internal tubular member 120 and which becomes the bottom wall portion 119t of the resin member 119 of the water-repellent filter member 200) of the resin sheet 84 is not in contact with the internal flange portion 120h. Thus, heat is unlikely to be transmitted to the aperture-closing portion 84k from the internal flange portion 120h, so that the aperture-closing portion 84k is held at a relatively low temperature so as not to cause mutual fusion of fibers of the porous, fibrous structure. The aperture-closing portion 84k therefore maintains the porous, fibrous structure of the resin sheet. As in the case of the water-repellent filter member 19 of Embodiment 1, the water-repellent filter member 200 of Embodiment 2 can maintain air permeability at the bottom wall portion 119t of the resin member 119.

While the present invention has been described with reference to Embodiments 1 and 2 and Modified Embodiments 1 and 2, the present invention is not limited thereto, but may be modified as appropriate without departing from the spirit or scope of the invention.

For example, Embodiments 1 and 2 and Modified Embodiments 1 and 2 are described while mentioning the internal tubular member formed of a metal material (stainless steel). However, no particular limitation is imposed on the material of the internal tubular member, so long as it is resistant to heat involved in forming the resin sheet into water-repellent filter member or the resin member. Examples of such materials include metal materials, such as stainless steel and aluminum; ceramics, such as alumina; glass; and heat-resistant resin materials, such as PTFE and polyimide.

In Embodiment 1, in order to hold the water-repellent filter member 19 formed of the resin sheet in the interior of the grommet 17, the internal tubular member 20 is inserted into the water-repellent filter member 19. However, when the tubular side wall portion 19s of the water-repellent filter member 19 has sufficient rigidity, the water-repellent filter member 19 may alone be singly inserted into the air through-hole 18 of the grommet 17.

Embodiment 2 mentions, as engagement portions, the through-holes 120c formed in the outer circumferential surface 120g of the internal tubular member 120. However, the engagement portions may assume the form of, for example, pits and projections formed on the outer circumferential surface of the internal tubular member by blasting, knurling, or the like.

In manufacture of the water-repellent filter member, Embodiments 1 and 2 and Modified Embodiment 1 use a female die member having heaters so as to heat the water-repellent filter member from a radially outside direction. However, no particular limitation is imposed on the heating method, so long as the sheet projectional-end portion (which corresponds to the bottom wall portion) of the resin sheet is not fused. Accordingly, heat may be applied from a radially inside direction; specifically, a heater may be provided in the rodlike portion of the male die member so as to increase the temperature of the rodlike portion.

In manufacture of the water-repellent filter member, Embodiment 1 and Modified Embodiment 1 use the male die members 52 and 62 having rodlike portions 52b and 62b assuming hollow, tubular forms. However, no particular limitation is imposed on the form of the rodlike portion, so long as the tip end of the rodlike portion is not in contact with the resin sheet. For example, the rodlike portion of the male die member may be such that a depression is formed on its tip end.

Embodiments 1 and 2 and Modified Embodiments 1 and 2 refer to oxygen sensors as waterproof instruments. However, the present invention is not limited thereto. The present invention can be applied not only to gas sensors represented by oxygen sensors, but also to electronic instruments and other waterproof instruments that employ water-repellent filters allowing air communication between their internal spaces and the exterior thereof.

This application is based on Japanese Application No. 2004-194383 filed Jun. 30, 2004, the above noted application incorporated herein by reference in its entirety.

What is claimed is:

1. A gas sensor comprising:
a gas detection element in contact with a reference gas via a first surface and in contact with a gas to be measured via a second surface opposite the first surface; and
a waterproof enclosure member defining, together with the gas detection element, an internal space to which the first surface of the gas detection element is exposed but the second surface of the gas detection element is not exposed;
wherein the enclosure member includes a waterproof grommet, enclosing at least a portion of the internal space, having an air through-hole extending therethrough, establishing air communication between the internal space and an exterior of the gas sensor, and formed of a rubberlike elastic material; and
the grommet has a water-repellent filter member fitted into the air through-hole thereof, allowing air communication between the internal space and the exterior of the gas sensor through the air through-hole, and preventing entry of water into the internal space through the air through-hole,
wherein the water-repellent filter member is formed from a resin sheet of a porous, fibrous structure having air permeability and water repellency, the filter member comprising:
a tubular side wall portion; and
a bottom wall portion closing one end of the tubular side wall portion,
fibers of the resin sheet being fused together at the tubular side wall portion so as to enhance rigidity thereof, and
at least a portion of the bottom wall portion maintaining the porous, fibrous structure of the resin sheet and thereby having air permeability.

2. A gas sensor comprising:
a gas detection element in contact with a reference gas via a first surface and in contact with a gas to be measured via a second surface opposite the first surface; and
a waterproof enclosure member defining, together with the gas detection element, an internal space to which the first surface of the gas detection element is exposed but the second surface of the gas detection element is not exposed;
wherein the enclosure member includes a waterproof grommet, enclosing at least a portion of the internal space, having an air through-hole extending therethrough, establishing air communication between the internal space and an exterior of the gas sensor, and formed of a rubberlike elastic material; and
the grommet has a water-repellent filter member fitted into the air through-hole thereof, allowing air communication between the internal space and the exterior of the gas sensor through the air through-hole, and preventing entry of water into the internal space through the air through-hole,
wherein the water-repellent filter member comprises:
an internal tubular member having a tubular form and allowing air communication therethrough past a first end thereof and a second end thereof; and
a closed-bottomed tubular resin member formed of a resin sheet of a porous, fibrous structure having air permeability and water repellency,
the resin member comprising:
a bottom wall portion closing the first end of the internal tubular member; and
a tubular side wall portion covering at least a portion of an outer circumferential surface of the internal tubular member, the portion being located adjacent to the first end of the internal tubular member,
fibers of the resin sheet being fused together at the tubular side wall portion so as to enhance rigidity thereof, and
at least a portion of said bottom wall portion of the resin member maintaining the porous, fibrous structure of the resin sheet and having air permeability.

3. A gas sensor according to claim 2, wherein the internal tubular member of the water-repellent filter member has an engagement portion formed on the outer circumferential surface thereof and adapted to engage with the resin member so as to prevent detachment of the resin member.

* * * * *